(12) United States Patent
Stein

(10) Patent No.: US 9,834,874 B2
(45) Date of Patent: Dec. 5, 2017

(54) TEXTILE FABRIC

(75) Inventor: Gabriele Stein, Elchingen (DE)

(73) Assignee: Pervormance International GmbH, Ulm (DE)

( * ) Notice: Subject to any disclaimer, the term of this patent is extended or adjusted under 35 U.S.C. 154(b) by 1229 days.

(21) Appl. No.: 13/389,145

(22) PCT Filed: Aug. 7, 2010

(86) PCT No.: PCT/EP2010/004853
§ 371 (c)(1),
(2), (4) Date: Feb. 6, 2012

(87) PCT Pub. No.: WO2011/015377
PCT Pub. Date: Feb. 10, 2011

(65) Prior Publication Data
US 2012/0157904 A1    Jun. 21, 2012

(30) Foreign Application Priority Data

Aug. 7, 2009 (DE) .......................... 10 2009 036 588
May 21, 2010 (DE) .......................... 10 2010 017 065

(51) Int. Cl.
| | |
|---|---|
| A61F 7/10 | (2006.01) |
| D04H 1/48 | (2012.01) |
| A61F 7/02 | (2006.01) |
| A61F 13/00 | (2006.01) |
| D04H 1/407 | (2012.01) |
| D04H 1/4374 | (2012.01) |

(Continued)

(52) U.S. Cl.
CPC ............... *D04H 1/48* (2013.01); *A61F 7/02* (2013.01); *A61F 13/00* (2013.01); *D04H 1/407* (2013.01); *D04H 1/4374* (2013.01); *D04H 1/4382* (2013.01); *D04H 1/49* (2013.01); *D04H 1/498* (2013.01); *D04H 1/541* (2013.01); *D04H 1/559* (2013.01); *D04H 1/64* (2013.01); *D04H 1/74* (2013.01); *D04H 3/00* (2013.01); *D04H 3/12* (2013.01); *D04H 3/14* (2013.01); *D04H 13/00* (2013.01); *A61F 2007/0214* (2013.01); *A61F 2013/00191* (2013.01)

(58) Field of Classification Search
CPC ...... A61F 13/00; A61F 13/00191; A61F 7/02; A61F 2007/0214
See application file for complete search history.

(56) References Cited

U.S. PATENT DOCUMENTS

| | | | | |
|---|---|---|---|---|
| 3,944,498 A | * | 3/1976 | Moyle .................. | A61K 8/4986 510/386 |
| 6,194,630 B1 | * | 2/2001 | Chihani ................. | A61L 15/24 156/308.2 |

(Continued)

FOREIGN PATENT DOCUMENTS

| | | |
|---|---|---|
| DE | 10232078 | 3/2004 |
| EP | 0 463 716 | 1/1992 |

(Continued)

*Primary Examiner* — Kaitlyn Smith
*Assistant Examiner* — Eunhwa Kim
(74) *Attorney, Agent, or Firm* — Studebaker & Brackett PC

(57) ABSTRACT

The invention relates to a textile fabric made of a fleece comprising a super absorbing activation, to a method for producing the textile fabric, to a covering surrounding the textile fabric, to a cooling system using the covering and to a covering designed as a cooling item.

10 Claims, 3 Drawing Sheets

(51) Int. Cl.
*D04H 1/4382* (2012.01)
*D04H 1/49* (2012.01)
*D04H 1/498* (2012.01)
*D04H 1/541* (2012.01)
*D04H 1/559* (2012.01)
*D04H 1/64* (2012.01)
*D04H 1/74* (2006.01)
*D04H 3/00* (2012.01)
*D04H 3/12* (2006.01)
*D04H 3/14* (2012.01)
*D04H 13/00* (2006.01)

(56) References Cited

U.S. PATENT DOCUMENTS

| | | | |
|---|---|---|---|
| 6,473,910 B2 * | 11/2002 | Creagan | A41D 13/0056 2/102 |
| 2002/0100106 A1 * | 8/2002 | Simmons | A42C 5/04 2/171.2 |
| 2003/0118854 A1 * | 6/2003 | Barson | B01J 20/28028 428/537.5 |
| 2004/0226077 A1 * | 11/2004 | Toth | A42B 3/10 2/411 |
| 2005/0118383 A1 * | 6/2005 | Cargill | A61F 7/02 428/68 |
| 2005/0130542 A1 * | 6/2005 | Klein | A41D 31/02 442/394 |
| 2009/0090018 A1 * | 4/2009 | Stein | A62B 17/005 34/60 |
| 2010/0137953 A1 | 6/2010 | Stein | |

FOREIGN PATENT DOCUMENTS

| | | |
|---|---|---|
| EP | 0 676 496 | 10/1995 |
| EP | 1 260 626 | 11/2002 |
| WO | 01/47456 | 7/2001 |
| WO | 03/012182 | 2/2003 |
| WO | 2004/016425 | 2/2004 |
| WO | 2004/105823 | 12/2004 |

* cited by examiner

TEXTILE FABRIC

This is a national stage of PCT/EP10/004853 filed Aug. 7, 2010 and published in German, which claims the priority of German number 10 2009 036 588.5 filed Aug. 7, 2009, and German number 10 2010 017 065.8 filed May 21, 2010, hereby incorporated by reference.

FIELD OF THE INVENTION

The invention relates to a textile fabric made of a fleece comprising a super absorbing activation, to a method for producing the textile fabric, to a covering surrounding the textile fabric, to a cooling system using the covering, and to a covering designed as a cooling item.

BACKGROUND OF THE INVENTION

Textile fabrics showing an absorbing activation are known from the hygiene field. The textile fabrics comprise an absorbing activation in the form of particles or the like, configured to absorb liquids and to bond them permanently. Here, the features of the so-called super absorbers used in textile fabrics of the prior art serve to considerably increase the capacity for absorbing liquids in diapers for children and adults and other absorbing hygiene products and to permanently bond the absorbed liquid.

For this purpose, single-use textile fabrics are known in the prior art, which comprise a carrier layer, for example made from fibrous cellulose or other fleece-like materials. So-called super absorbers are incorporated on or in these carriers in the form of particles. Due to only moderate stress of the single-use article no extensive connection is established between the super absorbing particles and the material of the carrier layer. The fixation of the super absorbing particles occurs for example by a loose sprinkling among the fibrous material or the layers of the respective article. Additionally, the above-mentioned single-use articles are designed such that they absorb and bond any liquids. Any release of the absorbed liquid is not provided and/or not desired in any case. Rather the purpose of the super absorbing, activated article is to provide a dry surface at all times and to permanently prevent the release of liquid from the article.

Due to the fact that the articles of prior art represent single-use articles not intended for repeated use no investments are made to lastingly connect the super absorber provided in the fabric with the carrier materials. Thus, under sufficient mechanical stress the particles easily separate from the fibrous fabric and collect preferably in the inner, lower-lying section of the article. The absorbing and/or desorbing features are significantly worsened.

Another use of particles comprising super absorbers is found in cooling. This utilizes the circumstance that cooling occurs by the release of liquids absorbed by the super absorbers and evaporating, due to the heat required for evaporation. The products of prior art using super absorbers for cooling show the problem, that they are embodied either as gel-accumulators, chambers filled with gel or made from gel, produced such that water or another liquid is filled into pockets, in which the super absorber is contained in the form of particles or crystals. However, prior to use, most of these gel-based products must be stored in the refrigerator or a freezer in order to work properly. The cooling effect is achieved here such that the gel pockets and/or the gel accumulators adjust to the temperature of the refrigerator or a freezer and maintain said temperature. The disadvantage of this use of the super absorber is frequently its high weight. The time necessary for the preliminary cooling of the accumulator and/or the gel pockets or chambers and the usually extensive process, (is) prone to errors, because the super absorbers, when arranged in fabric, only turn into gel upon treatment with water. Furthermore, the products of prior art show only short cooling periods.

When the super absorbing material is arranged on fabrics and/or integrated therein the disadvantage is that the fabrics require a longer period of time until the water is completely absorbed, remain wet for a long time, and drip. Sometimes, the gel formed in the fabrics or the water also penetrates the fabric and leads to a wet or slimy effect at the outside of the fabric, which limits the permanent use of the fabrics. Additionally, it takes quite some time until the textile product is charged with water and dried to such an extent that it can be used without the objects cooled and/or the surfaces or body parts are moistened.

Many of these products cannot be used after one or just a few applications, change their appearances or their interior begins to disintegrate. Most of all, the products cannot be washed and frequently not be dry cleaned, either, which also limits their application. Some products attempt to address this via textile features, which however results in a worsened evaporation process and/or poorer cooling effects.

Based on prior art, the objective of the present invention is to provide a super absorbing activated textile fabric, suitable for cooling, and objects made therefrom which are applicable quickly, simply, lastingly, and repeatedly, as well as over an extended period of time.

This objective is attained in the several objects suggested by the invention.

SUMMARY OF THE INVENTION

Firstly, a textile fabric is suggested, which is reusable, can be charged with liquids and thus be activated, and acts in a cooling manner during discharge, i.e. for example by evaporating or vaporizing the charged liquid and/or the liquid components, from a fleece comprising a super absorbing activation, which is suitable for a repeated charging and discharging of a liquid and with particularly the discharging process serving for cooling purposes and with the textile fabric comprising in the dry state, not charged with liquids or liquid components, a mass per area ranging from 50 to 1500 $g/m^2$, preferably from 50 to 700 $g/m^2$. A super absorbing activation is understood here such that a material forming a super absorbing activation is provided in a solid, dissolved, gel-like, or liquid form which is fixed in, at, or on the textile fabric, capable to absorb liquids by a multitude of its own weight. Liquids in question here, include for example water or saline solutions as well as mixtures of water, alcohol, or other adjuvants or additives. The super absorbing activation of the textile fabric according to the invention can be performed by integrating so-called super absorber polymers (SAP), which either coat the surfaces of the textile fabric and/or the fibers or filaments or which are incorporated in the textile fabric, for example glued, woven, spun, or connected to the textile fabric in any other suitable fashion. Here, the super absorbing activation shows a stable, permanent bond with the fleece and/or the fibers or filaments forming the fleece, or represents an integral component of the fleece, and/or the fibers and/or filaments form the fleece.

Here, the SAP-polymers not only serve for a one-time absorption and release of liquid. The speed and even distribution of the absorption and release of liquids as well as the amount of liquids absorbed can be controlled by the type of introduction as well as the shape, size, structure, and composition of the polymers and/or other polymer components. This way, suitable cooling parameters can be adjusted and/or defined for the respective purpose for use, and the cooling performance as well as the cooling effect achievable with the textile fabric can be controlled.

Therefore, the goals and the field of application of the textile fabric according to the invention are clearly distinguished from the single-use articles of the prior art, because the latter are not suitable or intended for repeated application or the use for cooling purposes. The prior art used for cooling purposes also fails to combine the above-discussed features of the present invention.

The invention achieves a reliable, lasting bond of the super absorbing activation, preferably embodied as super absorbing polymers (SAP), with a fleece, thus avoiding, among other things, the separation or collection of super absorbing polymers at the fabric and/or material surfaces limiting the fleece so that a respectively slippery or slimy effect, created by insufficient polymerization of the super absorbing polymers and the monomers present thereby, is permanently avoided at the outside of the boundary fabric and/or material. This is avoided in the textile fabric according to the invention such that an almost complete polymerization of the super absorbing polymers is targeted and/or achieved. Any still present monomers are removed from the textile fabric in a subsequent separation step. Here, the activation is achieved in such a stable fashion that it also allows an extended period of use of the textile fabric and/or the object carrying and/or comprising the textile fabric (such as a cover). The bond of super absorbing polymers and fleece and/or textile fabrics occurs here in a chemical, mechanical, or thermal process.

Additional potential applications for the textile fabric according to the invention result. The use of the textile fabric according to the invention, for example in clothing, is here possible without any problems because the life span of the super absorbing activation in the textile fabric according to the invention and/or the fleece forming it and/or provided therein is extended such that a relatively long-lasting use of the clothing is possible with an (almost) consistent cooling effect and performance without any problems.

The suggestion according to the invention also allows other fields of application, in which particularly an article is as hygienic as possible. Due to the fact that even under extended use the super absorbing activation and/or the super absorbing polymers forming the super absorbing activation remain in the fleece in a suitable fashion (as described above), the polymer particles abstain from separating from the fleece, as is common in products of the prior art and any monomers still present cannot plug the pores of the fabric covering the fleece and/or the textile fabric. This is advantageous here, due to the fact that perhaps water vapors or water can penetrate these boundary layers in order to allow the effect according to the invention to occur, and no barrier effect and thus no compromise of the effectiveness develops. Additionally, the appearance of the fabric remains lastingly unchanged.

A super absorbing activation is also represented, for example, when a pad comprises a super absorber or the textile fabric is penetrated with super absorbers embodied in a fibrous fashion. Charging the textile fabric with a liquid occurs here, for example, by immersing the textile fabric and/or an object encasing the textile fabric into the liquid, and here particularly water, saline solutions, and/or mixtures of water, alcohol, and/or additives or adjuvants. In addition to the immersion into the respective liquid, initially also a superficial moistening may occur, for example by spraying or pouring the respective liquid, in order to charge the textile fabric. During the moistening and/or the penetration said liquid is quickly, i.e. within a few seconds, absorbed and reversibly stored by said super absorbing activation.

Here, the textile fabric according to the invention is embodied such that the super absorbing activation is capable to perform an extended release of the liquid. During said release of liquid it is evaporated and consequently a cooling effect occurs. This is caused by heat and/or thermal energy being removed from the body or object to be cooled in order to evaporate the water and/or other liquid and thus it is cooled. The textile fabric according to the invention is here embodied such that repeated charging and discharging with liquid can occur without the super absorbing activation showing any considerable loss in function. This is achieved by a permanent bond of the textile fabric and the super absorbers via a chemical, mechanical, or thermal process.

The textile fabric according to the invention is particularly lasting and stable in order to provide it for a range of application as wide as possible, showing a weight per area ranging from 50 $g/m^2$ to 1500 $g/m^2$. Here, the values exclusively relate to the weight of the untreated, preferably dry textile fabric, i.e. without any liquid charge and without the weight of any potentially encompassing, enclosing, and/or covering materials enclosing the textile fabric. While the textile fabric, having a comparably low weight per area, is particularly suited to finish objects carried at the body or in clothing which shall not hinder the wearer, a textile fabric having a weight per area up to 700 $g/m^2$ and more is particularly suitable to absorb large amounts of liquids and release this large amount again during the intended release of liquids. The textile fabrics with a heavy weight in reference to their area form cover materials, for example, used for cooling larger objects, such as in case of fires, very high temperatures, or the like. The heavy weight in reference to the area is accompanied by a particularly lasting embodiment of the textile fabric so that it shows a considerably improved mechanical stability and is therefore also suitable for higher stressed applications, for example in the sanitary or medical field as well as for mobile applications, for example the covering of vehicles or devices as well as large machines. However, in general there is the chance to use the textile fabric according to the invention for all applications intended, not exceeding the above-mentioned limits.

In addition to the two major fields of application, which are particularly characterized in the weight per area on the one hand ranging from 50 $g/m^2$ to 700 $g/m^2$ and on the other hand in a weight per area ranging from 500 $g/m^2$ to 1500 $g/m^2$, the invention includes other suggestions, of course, ranging from 50 $g/m^2$ to 100 $g/m^2$, 100 $g/m^2$ to 200 $g/m^2$, 200 $g/m^2$ to 300 $g/m^2$, 300 $g/m^2$ to 400 $g/m^2$, 400 $g/m^2$ to 500 $g/m^2$, as well as from 500 $g/m^2$ to 600 $g/m^2$, 600 $g/m^2$ to 700 $g/m^2$, 700 $g/m^2$ to 800 $g/m^2$, 800 $g/m^2$ to 900 $g/m^2$, as well as from 900 $g/m^2$ to 1500 $g/m^2$, or more. The weight of the textile fabric per area may also be freely selected by the user from the above-mentioned ranges of value depending on the field of application of the textile fabric and/or adjusted within or outside said ranges of values.

The above-mentioned weight in reference to area, amounting in the textile fabric according to the invention from 50 $g/m^2$ to 1500 $g/m^2$, relates to the entire textile fabric, however without any surrounding or covering materials.

In this context it is considered advantageous for the source and/or crude fleece to show a weight per area ranging from 50 $g/m^2$ to 120 $g/m^2$. The fleece component in the textile fabric ranges here for example from 10% to approximately 25%, depending on the ultimate embodiment of the textile fabric with regards to weight.

In this context it must be mentioned that the relative values stated above and in the following shall not be interpreted as limiting the respectively mentioned example but of course the invention may also show a variant of a fleece portion in the textile fabric according to the invention with the weight in reference to the area perhaps amounting up to 1500 g/m².

Of course, according to the invention there is also the option of the textile fabric to comprise several layers of fleece. The component of fleece then increases, for example doubles or triples, depending on the number of layers of fleece being provided in the textile fabric. Here it is also possible for the layers of fleece to be separated by layers provided on top or therebetween and showing non-absorbing or lesser absorbing materials or the like.

Via the weight of the fleece in reference to the area ultimately the suitability of the textile fabric is determined for its respective field of application. For example, an increased weight per area also affects the ultimate thickness of the fleece and/or the height of the fleece material. The range of values stated relates to the weight of the fleece per area, with the other components of the textile fabric according to the invention here remaining unconsidered, such as the materials forming the super absorbing activation, potential overlays, or carrier layers of the textile fabric, as well as other additives, such as adhesives and other functional activators or substances. They form the textile fabric in coordination with the fleece, and define its weight per area. Particularly for the use in textile materials, medical products, or products for cooling bodies or body parts, the weight of the fleece per area ranges preferably from 60 g/m2 to 100 g/m², with these values exceeded or fallen short, if applicable. A weight per area amounting to 80 g/m² has proven particularly beneficial.

The thickness of the fleece used in the textile fabric is independent from the ultimate weight per area and/or the mass per area, with the term thickness in the present case being equivalent to the term height used in the field of textiles, stating the height and/or a vertical extension of the fabric and/or the fleece web. It beneficially ranges from 0.1 mm to 30 mm, with the thickness/height of 1 mm to 10 mm being preferred and particularly a thickness/height of 6 mm to 9 mm, preferably of 4 mm to 7 mm proves to be beneficial. The above-mentioned ranges of thickness/height of the fleece in the textile fabric are primarily determined by the ultimate use of the finished textile fabric comprising the fleece. For example, thicknesses of fleeces ranging from 0.1 mm to 10 mm are used suitably in textiles or in the above-mentioned (medical) cooling products, while mechanically highly stressed textiles potentially subject to the risk of tearing, such as covering tarps or the like, show a greater thickness in order to ensure an appropriate life of the textile fabric. Additionally, in cooperation with the appropriately selected super absorber and its amount used and/or its respective portion by volume, the thickness/height determines the absorption capacity for the liquid and/or the amount of liquid absorbed. Of course, in a thicker/higher fleece there is the option to store more liquid than in a fleece showing only a few millimeters of thickness. Additionally, the thickness/height of the fleece decides its application. The thickness/height of the fleece is also determined by the situation of installation in a cover, for example a piece of clothing, a medical article, or a cover tarp. Here, the arrangement of a cover, surrounding the textile fabric and limiting it, may further reduce the thickness/height of the fleece. For example, the thickness/height of a source fleece may be reduced such that ultimately the textile fabric comprising the fleece shows one or more boundary layers or the like compressing the fleece inlay and perhaps partitioning it in order to this way reduce the overall thickness/height.

It is considered advantageous for the fleece to comprise reinforcing fibers, which stabilize and improve the overall structure of the fleece. The reinforcing fibers comprise the same or a similar material as the rest of the fleece, however they are essentially aligned in the fleece due to mechanical post-processing of the fleece and here particularly due to mechanical needling, for example. Here, it is provided that reinforcing fibers essentially penetrate the thickness/height of the fleece. However, it is provided here, that the respective reinforcing fibers are kept from penetrating the fleece entirely, thus form a connection between the exterior surfaces of the fleece but penetrating only half of the fleece or perhaps ⅔ or ¾ of the fleece. Of course, there is also the possibility for a penetration of the fleece by the reinforcing fibers up to almost the entire thickness/height of the fleece. Here, values for the penetration of the fleece are achieved up to 100%. A very strong needling is not and/or not yet targeted, though, in order for sufficient pores and openings to remain in the fleece for coating and finishing. The needling process also reduces the thickness/height of the fleece, perhaps. During the needling process, a structure, for example a beam or a bar provided with needles, hooks, or jets, is periodically pressed into and/or onto the fleece, this way further reinforcing the fibers. During the oppression, the needles/jets partially penetrate into the fleece, however only to a predetermined depth, and here entrain a portion of the fibers of the fleece and align them. These fibers then form the reinforcement fibers, which penetrate the fleece from the side at which the needles/jets are pressed into the fleece and/or pressed thereupon. Here, the needles/jets may show a structuring in the form of barbs or the like in order to further improve the needling process. The portion of reinforcement fibers provided in the fleece depends on the number of needles/jets of the impinging area used, and/or on the intensity and duration of the needling process. In addition to needling via needles, there is also the option for the reinforcement of the fleece to occur in a so-called water jet—reinforcement method. Here, similar to the impingement of the fleece with needles, for example via nozzles fine water jets are inserted into the fleece and also cause a penetration of the fleece by individual fibers forming the reinforcement fibers of the fleece material.

A preferred further development of the textile fabric according to the invention provides that a mechanical, chemical, or thermal interlacing and/or needling occurs of individual fibers and/or filaments of the fleece with each other. Here, it shall be pointed out that a fleece is formed from loosely contacting fibers, which are or become connected to each other. Fleeces or fleece materials are characterized in the presence of fibers arranged arbitrarily in the fleece material. For the ultimate formation of the fleece and/or the fleece material the above-mentioned interlacing and/or needling of the individual fibers and/or filaments of the fleece with each other is required. Furthermore, the terms fibers and filaments are always used jointly and as synonyms. In the context with the present invention, fibers and filaments are considered thin oblong formations with a defined diameter formed from polymers. Contrary to filaments, which in general may be formed with an infinite length, fibers show a limited length.

Mechanical, thermal, or chemical treatments are suitable as reinforcement methods for fleeces and/or fleece materials, such as reinforcement by needling or by water jet reinforcement/needling. Additionally, during the course of a chemical reinforcement, there is the chance to add binders or adhesives to the crude fleece and/or the initial fleece material, which then perform or ensure the connection and/or reinforcement of the fibers of the fleece. In addition to the above-mentioned mechanical or chemical methods or parallel thereto there is also the option of reinforcing the fleece by thermally impinging the crude or initial material and/or the crude or initial fleece. Here, it is provided that the fibers are contacted by heated or hot air and/or a heated gas flow. This leads to a superficial melting of the fibers and/or the fibrous material and subsequently to an adhesion of the liquefied jacket material of some closely neighboring fibers. Here, it is decisive that the gas flow and/or the duration of the impingement are adjusted such that no complete melting of the fibers occurs, which would result in them tearing, but only the liquefaction of the exterior layers of the fibers shall occur. In addition to the impingement with heated gas, providing that the crude fleece is guided between heated rollers and, at the surfaces of the rollers, initially a superficial softening of the fibers occurs and subsequently their adhesion to each other. Here, simultaneously a reduction of the thickness of the fleece can be performed.

Depending on the source material for the fleece and the respective chemical features of the fibers, in addition to the use of a heated gas flow, there is also the option to perform the temperature impingement of the fibers via a steam flow. The effect is similar to the above-described one. The ultimate structure of the fiber, having a fiber core and a fiber jacket, can be predetermined via the chemical features of the fibers and/or already in the production process. Here, the fiber can be adjusted or embodied such that the fiber core shows a different melting temperature in reference to the fiber material. This feature of the fiber can then in turn be used in the thermal reinforcement of the crude fleece, namely when only a melting of the fiber jacket shall be performed by a respective temperature impingement, however not a melting of the fiber core.

According to the invention it is provided that the fleece is embodied as a nano-fiber or micro-fiber fleece. Here, the fleece can be formed from finest fibers or finest filaments. The classification of the fleeces into respective material categories occurs here similar to and/or depending on the fineness and/or the diameter of the fibers forming the fleece. In the following, all discussions relate to fleeces, regardless if fleeces are used made from nano-fibers or micro-fibers. Here, it shall be stated that the term fleece includes both an embodiment as a fleece made from nano-fibers or microfibers, without it being specifically mentioned. The term fleece therefore represents a generic term, covering all other types of fleeces, without them being explicitly mentioned. The same applies for the finest fibers and/or finest filaments used in the latter most described preferred embodiment. They only represent terms defined by the fineness and/or the diameter of the fibers or filaments and are also included in the generic term fiber and/or filament. When in the present description the term fibers and/or filaments are used, they represent equivalently finest fibers and finest filaments without being required to explicitly stating said fact. In the following, the importance of the fineness of fibers is discussed separately.

Preferably, the nano-fiber fleece is produced from finest fibers and/or finest filaments having a diameter of less than 10 µm, particularly preferred less than 1 µm, and preferably produced by way of electrostatic spinning. The fibers or filaments of the nano-fiber fleeces preferably comprise thermoplastic and hydrophilic or hydrophilyzed polymerisate, which can be spun when melted, particularly comprising polyurethane. Particularly when a nano-fiber fleece is used the high water and/or fluid-retention capability of the fiber per se is utilized, which is increased to a beneficial synergy by the use with the super absorber.

The textile fabric according to the invention focuses on allowing a multiple and/or repeated absorption and controlled release of liquids. This means that the super absorbing activation must be bonded permanently with the textile fabric. In order to ensure a permanent connection between the textile fabric and/or the fleece arranged in the textile fabric as well as additionally or alternatively the fibers or filaments of the fleece the super absorbing activation must be bonded with the respective components of the textile fabric in a non-abrasive fashion and mechanically stable. Alternatively, this is particularly achieved such that the fibers or filaments of the fleece in their entirety or at least partially comprise super absorbing polymers (SAP), i.e. formed from SAP-fibers/SAP-filaments.

As mentioned above, another advantage of the super absorber polymers bonded with the fleece and/or connected to the fibers or filaments comprises that a relatively homogenous and fine distribution of the super absorbing polymer is achieved and stabilized on the respective surfaces in the fleece. By the homogenous distribution of the super absorbing polymer in the fleece and/or in or on the fibers or filaments any mutual covering of the polymers is also prevented, which would coincide with reduced water absorption.

A preferred embodiment of the textile fabric according to the invention provides that the fleece and additionally or alternatively the fibers or filaments forming the fleece comprise an impingement with at least one super absorbing activation means, with the portion of the impinged super absorbing activation means at the fleece and/or the fibers or filaments ranges from 0 to 800 percent by weight in reference to the weight of the fleece in reference to its area. Here, it has shown that the fleece is capable to absorb an amount of activation means up to eight times its weight. The features of the fleece can be adjusted appropriately via the portion of super absorbing activation means. Via the portion of the super absorbing activation means the features of the fleece and via them those of the textile fabric can be adjusted appropriately. Such an adjustment occurs depending on the ultimately provided purpose for use of the textile fabric, with it always being kept in mind that for example for the use of briefly cooling, among other things persons or body parts, a lower impingement with super absorbing activation material is sufficient, while, in the interest of an extended release of liquid and thus a lasting cooling, a higher impingement with super absorbing activation means is recommended. Based on the above-mentioned values for the area weight of the fleece by weight used in the textile fabric, for example using an 800% impingement of the fleece with a weight in reference to area of 120 g/m$^2$, an ultimate weight of the fleece of 1.080 g/m$^2$ is yielded.

In an embodiment of the textile fabric according to the invention considered beneficial it is provided that, in order to connect the fleece and/or the fibers or filaments with the super absorbing activation means, an impingement of the fleece or the fibers or filaments is provided with an adhesive, particularly on a polyacrylate base. In this context it is provided that the portion of the impinging adhesive at the fleece ranges from 0 to 85 percent by weight in reference to the weight of the fleece in reference to area. The impingement with adhesive leads to a permanent, abrasion-resistant and mechanically stable connection of super absorbing activation means and textile fabric, because here the direct bonding occurs between the fleece and/or fibers or filaments of the fleece and super absorbers. The adhesives embodied based on polyacrylate have proven particularly lasting, even after repeated use and/or a more or less intensive cleaning of the textile fabric, for example after it becoming soiled during use, and thus ensure a long life of the textile fabric and/or a long-lasting bond of the super absorbers in the textile fabric.

The strength of the shape of the fleece can also be influenced by a high component of adhesives. Here, with an elevated content of adhesives an appropriately formed part can be developed from the fleece, which can be activated and is strong with regards to its shape, which can stably maintain its shape, even after several washings and/or cleaning processes, in particular.

In the interest of particularly close bonds between the fleece and/or the fibers or filaments forming the fleece, and the super absorbing activation means it is recommended for the fleece and/or additionally the surface of the fibers or filaments to comprise a coating with the super absorbing activation means and/or adhesive. The impinging of the fleece, its surface, and/or the fibers or filaments with the super absorbing activation means and/or the adhesive can here occur, in addition to the spray method using respective pressures and nozzle sizes, in a so-called foulard method. Here, the crude fleece and/or the fibers forming the fleece are pulled through an adhesive and/or a super absorbing activation means or a bath comprising a mixture of the latter-mentioned substances and here moistened at all sides with the respectively composed solution. The super absorbing activation means and/or the adhesive then stick to the surface of the fleece and/or the surfaces of the fibers or filaments. The part of the solution not bonded to the fleece and/or the fibers is pressed out of the fleece and/or the fibers or fiber strands by way of calendering. Subsequent to the foulard process an impingement of the pre-treated fleece and/or the pre-treated fibers or also an appropriately embodied fiber strand may occur with a super absorbing activation means, unless it was not included in the foulard solution. The still sticky surface of the fleece and/or the fibers is here contacted with the super absorber provided in the form of a powder or particles, for example sprinkled on, or the super absorber is blown onto the fleece web and/or the fibers of the fibrous strands. The adhesive subsequently cures and bonds the fibers permanently to the super absorber. In addition to the use of a foulard method, there is also the option to spray a solution comprising only adhesives or adhesives and super absorbing activation means onto the fleece via the arrangement of appropriate nozzles and/or to impress them or to blow them on. In addition to an appropriate treatment of the fleece of course it is also possible to yield the coating of the fibers or filaments forming the fleece in a spray method, with here also a spray solution may be used, which comprises both adhesives as well as super absorbing activation means or only adhesives. There is the option for the subsequent adhesion of super absorbers to occur on the spray-coated fleece and/or the spray-coated fibers. In order for the adhesive to cure and for a further improvement of the bond between the super absorbers and the fleece and/or the fibers curing of the coated carrier material, an interlacing of the adhesive for example via UV-light, or sintering or baking may also occur or any other thermal treatment of the fibers or the fleece. The above-mentioned procedure is advantageous in that in addition to a particularly intimate and thus lasting bond of the fleece and/or its fibers or filaments of the fleece to the super absorbers and/or super absorber polymers also a homogenous distribution of the super absorber in the textile fabric is yielded, which in turn leads to an improved, particularly rapid absorption and homogenous release of the liquid. By adjusting appropriately suitable concentrations of super absorbing polymers for the coating, ultimately the amount and distribution of super absorbing polymer on the fibers or filaments and/or the fleece can be controlled. The super absorbing polymers provided, for example in the form of crystals, can here be arranged, optimally distanced, at the fibers/filaments and/or in the fleece so that here their maximal and rapid swelling can be ensured. A permanent bond of super absorber polymers and fibers/filaments and/or fleece is also achieved because an adhesion of the super absorbing polymer is performed directly at the fiber. The super absorbing polymers are therefore fixed components of the fleece and not loosely arranged and for example only fixed in their position with the help of adhesives. Thus a flexible material develops, which is formed from a compound of super absorbing activated fibers/filaments or super absorbing polymer fibers and in which the super absorbing polymers are fixed permanently at their location.

A preferred further development of the textile fabric according to the invention provides that the fibers or filaments ultimately forming the fleece show a grist of yarn of 0.1 to 20 dtex [gram/10,000 meter]. Via the respective grist of yarn, subsequently the fleece features are also defined. For example, there are nano-fiber fleeces made from fibers or filaments with a grist of yarn of less than 0.3 dtex, while micro-fiber fleeces show a grist of yarn of 0.5 to 0.7 dtex. The grist of yarn drops with increasing weight per length and ultimately the diameter of the filaments and/or fibers increases. Additionally, via the grist of yarn of the fibers or filaments forming the fleece the ability of the textile fabric to accept a super absorbing activation means is also determined. Due to the relative large surface of fleeces with fibers of small diameters, i.e. with relatively low weight per length, the option increases to arrange super absorbing activation means and thus the ability to absorb liquids. With reducing grist of yarn, i.e. with increasingly growing diameters of the fibers, with an increasing robustness of the fleece the chances fall for arranging additional super absorbing activation means on the surface of the fibers. Therefore, there is the option to select from a multitude of differently designed fleece materials the one best suited for the intended purpose, in order to then produce the textile fabric according to the invention.

It is considered beneficial for the fibers, groups of fibers or filaments, which as the generic term represent any fibers, groups of fibers, or filaments of different grist of yarn, to be formed from natural polymers, particularly based on cotton, bamboo, hemp, cellulose, mineral fibers, or from artificial polymers, particularly thermoplastic polymers, preferably polyethylene, polyamide, polyester, or polypropylene, or from polyurethane, polyvinylchloride, artificial silk—acrylic fibers, or also from biotechnologically produced polymers and/or mixtures or waste fibers of the above-mentioned polymers. In this context it is also considered advantageous for the fleece to be formed from a mixture of different fibers, groups of fibers, or filaments in order to here provide a particularly adjustable and/or multi-purpose textile fabric. It has proven beneficial for the mixture to comprise from 25% to 100% polymer fibers, from 0% to 20% waste fibers, and/or 0% to 10% low-melting polymer fibers. Here, the low-melting polymer fibers comprise particularly thermoplastic polymers such as polyethylene, polyamide, polyester, or polypropylene and provide, due to the low-melting features, an improved bonding of the fleece after the performance of a thermal curing process for the fleece. The above-mentioned use of fibers or filaments made from natural polymers and here particularly of polymers based on cotton, bamboo, hemp, or cellulose is advantageous in that these fibers, depending on the treatment of the respective polymer itself, show an absorbing features, which is then further improved by the addition of super-absorbing activation means, which results in an even more beneficial initial situation for the absorption of liquids. The use of artificial polymers as well as biotechnologically created polymers offers the advantage that it is possible to adjust the features of the fibers or filaments and/or the fleece formed therefrom particularly precisely and focused on the application. By the suitable selection of polymer fibers it can also be ensured that only a small portion of the liquid absorbed in the textile fabric adheres to the surfaces of the fibers and cannot be absorbed by the super absorbers. The suitable selection of polymers and the structuring of the ultimately formed fibers adjustable thereby can also contribute that the liquid filled into the textile fabric is guided by the fibers to the super absorbers and/or super absorbing articles adhering to the fibers and/or connected to said fibers, and is absorbed by them.

The fibers, groups of fibers, or filaments used preferably show no uniform grist of yarn. Rather, the above-mentioned fibrous materials are formed from groups with variable portions of fibers, groups of fibers, or filaments with in turn different grist of yarns each. The grist of yarns of the individual fibers can range here preferably from 0.1 dtex to 20 dtex. The embodiments and features of the fleece can be defined via suitable combinations of various fibrous materials and/or fibers with different grist of yarns.

An advantageous further embodiment of the textile fabric according to the invention provides for the fibers or filaments to be present in the form of two-component fibers. This particularly relates to a mixture of two polymers with different melting temperatures, particularly selected from a group comprising polyethylene, polyamide, polyester, polyurethane, and polypropylene, with the group can be arbitrarily expanded by the addition of other polymers, proven suitable and having an appropriate melting behavior. By the use of polymers with different melting temperatures additionally the features of the fleece being precisely adjusted when formed from the respective fibers. Additionally, in a thermal curing process, the ultimate cohesion and/or the curing of the fleece can be adjusted to nearly any degree. Via the portion of different polymers additionally a textile fabric can be provided adjusted to the respective purpose for use. In general, the invention also comprises textile fabrics in which the fibers or filaments only comprise one (homogenous) polymer. This polymer is here taken from the above-mentioned group. Of course, it is also possible to select the fibers and/or filaments of the nano-fleece and/or micro-fleece from the above-mentioned group.

It is considered beneficial in the sense of the invention for the textile fabric to comprise fibers or filaments formed by way of dry spinning, wet spinning, melt spinning, matrix spinning, or electro-spinning. Here, it is provided that a super absorbing activation of the textile fabric or the fleece formed from the fibers or filaments occurs prior, during, or after the spinning process. In wet spinning, the production of the fibers occurs from a respective polymer solution, which may comprise one or more of the above-mentioned polymers. This polymer solution is sprayed via nozzles into a precipitation bath of a solvent or a mixture of solvents, causing the polymer and/or the mixture of polymers to precipitate and form a fiber. In dry spinning, dissolved polymers are used as well, and extruded from a nozzle. The fibers and/or filaments formed coagulate in an air or nitrogen atmosphere and the solvent for the polymers evaporates here. The dry spinning method is suitable for polymers soluble in highly volatile solvents. In melt spinning the polymers are molten and pressed through one or more nozzles. Polymer fibers form upon exiting the nozzle, which are wound onto a mandrel or bobbin and can be provided for the subsequent formation of fleeces. Additionally, there is the option to directly apply the polymer fibers or filaments emitted from the nozzles onto a carrier and here to form the fleece. Depending on the embodiment of the nozzle and/or in case several nozzles are given, there is also the option to express different polymers simultaneously from several nozzles and thus forming a fleece comprising different polymers and/or fibers or filaments made from different polymers. This way, the features of the fleece can also be adjusted. Another way to form particularly thin fibers from polymer solutions, in particular, is provided in the so-called electro-spinning method. Here, the polymer solutions are treated in an electric field. The electro-spinning method is suitable for the formation of nano-fibers with diameters smaller than 1000 nanometers. Such fibers are then suitable for the formation of nano-fiber fleeces. Depending on the selection of the suitable spinning method an integration of the super absorbing activation can occur into the textile fabric and/or the fleece, prior, during, or after the spinning process. When a super absorbing activation and/or its implementation prior to the spinning process is given, an impingement of the respectively used polymer solution occurs with a super absorbing polymer material and the subsequent spinning of the polymer solutions formed this way. In a super absorbing activation during the spinning process, for example in a bath of the solvent, when a wet spinning method is used, a super absorbing polymer or another respectively super absorbing activation means may be introduced. They are then bonded with the fibers forming during the precipitation of the polymer solution in a precipitation bath. In a melt spinning method, in addition to the introduction of super absorbing activation means into the polymer solution to be jetted, there is also the option to provide an additional nozzle, via which the super absorbing polymer and/or another activating means is ejected together with the polymer solution and applied onto a respective carrier web. This is advantageous in allowing here to introduce the super absorbing activating means and here particularly super absorbing polymers directly and mechanically into the fleece forming and anchoring them to the fibers or filaments of the fleece during the stacking process.

It is considered advantageous for the super absorbing activation to occur by at least one super absorbing polymer introduced onto or into the fibers or filaments and/or into the fleece. Additionally and/or alternatively there is also the option for the fibers or filaments to be formed entirely or partially from at least one super absorbing polymer. A respective embodiment of the textile fabric then develops, for example when as explained above a co-extrusion of super absorbing polymer and fibrous polymer is performed. The same applies when the super absorbing polymers are mixed into the polymer solutions from which the fibers and/or filaments are formed. Of course, by using appropriate chemical finishing of the super absorbing polymers, if applicable, it is possible that the formation of fibers also occurs from super absorbing polymers in the above-mentioned spinning methods.

The super absorbing polymer is advantageously present in the form of particles, which beneficially show a diameter from 45 to 875 µm, particularly from 326 to 674 µm, preferably however from 400 to 500 µm. The advantage of a homogenous distribution of diameters and/or a clear fractioning of the particles is, on the one hand, an option provided thereby to relatively homogenously equip the fibers and/or fleeces with super absorbing polymers, on the other hand this way the absorption-active surface provided by the particles can be defined and precisely adjusted to the respective purpose for use. The improved fractioning improves the capacity and speed for absorbing liquids, which is here realized by a homogenous SAP-distribution and the polymer particles or crystals absorb liquids equally fast and in equal amounts without mutually shielding each other from the liquid to be absorbed and/or separating each other from the supply of liquids.

In another variant according to the invention it is provided that the particles particularly show a diameter from 50 µm to 150 µm. These considerably smaller particles show particular advantages, especially in the cooperation with micro-fibers and nano-fibers, produced in an electro-spinning method, for example. The cooperation of the much finer fibrous material of the micro-fibers or nano-fibers with the smaller super absorbing polymer particles in the range stated considerably facilitates the hydrophilic effect of the textile fabric, on the one side, but also the charging and/or discharging speed, on the other side. Here, the super absorbing polymers are sufficiently small for not resulting in any gel-blocking effect, thus certain parts of the super absorbing materials not participating in the water storage. Simultaneously, such a mechanically stable bonding is provided that the super absorbing polymer particles remain at the fibrous material with good quality. Here, too, the smaller diameter of the particles is beneficial. The use of the particles with smaller diameters is here not limited to micro-fibers or nano-fibers.

The diameter preferably chosen for the particles therefore relates to an equivalent diameter which can be determined by the particles passing a sieve based on the width of the holes of the sieve. It is considered beneficial for a mixture of particles to be used having different diameters. By using such mixtures, differently sized clear spaces in the body of the fleece forming due to the arbitrary stacking of fibers and/or filaments can be equally filled with the particles and thus an exclusively homogenous distribution of the liquid in the fleece and/or the textile fabric is ensured. It has been shown advantageous for the particles to be embodied cubic, rod-shaped, polyhedral, spherical, rounded, angular, needle-shaped, flaky, or fibrous or the like and here particularly to be provided in the form of powders, spheres, flakes or also as fibers or molecular and/or particle chains. The latter embodiment of the particles depends on the selection of fibers or filaments used and/or on the ultimate purpose for use of the textile fabric. For the selection of the respective particle form the method is also deciding by which the bonding between the super absorbing polymer articles and the fibers and/or filaments or the textile fabric and/or the fleece used in the textile fabric shall occur. For example, in a purely mechanical bond of particles and fibers or filaments and/or fleece a rod-shaped, needle-like, or polyhedral form of the particles may be preferred, while in case of gluing and/or superficial adhesion of the particles at the fibers or filaments and/or the fleece a spherical, flaky, or fibrous or needle-shaped embodiment of the particles might seem beneficial, because here a greater surface moistened and/or contacted by the adhesive agent is provided. In general, however, any potential shapes of particles can be used for all fibers/filaments and/or forms of fleeces and production processes.

In another further development of the invention considered beneficially it is provided that a super absorbing polymer represents a chemically interlaced co-polymer made from acrylic acid and one of its salts, particularly sodium acrylate. From these components long chains form in a polymerization reaction, which are interlaced by additionally inserted bonding means to form a loose but water-insoluble bundle of molecules. Any interlacing of the co-polymer can here also occur after the bonding of super absorbing source polymer (precursor) and the textile fabric and/or the fibers or filaments. The interlacer is then only added to the treated material after a respective mixing of super absorbing polymers and fibers and/or filaments or textile fabrics and/or fleeces. During the subsequent interlacing and/or after the polymerization reaction of the super absorbing polymer, beginning after the interlacer was added, a close bonding develops between the super absorbing polymer and the textile fabric and/or the fibers or filaments and/or the fleece formed therefrom. In this context it is considered beneficial for the super absorbing polymer and/or the super absorbing polymer particles to surround and/or to encase the fibers or filaments or alternatively to entirely or at least partially coating the fibers or filaments, i.e., over a certain longitudinal section. This embodiment of the fibers or filaments has proven beneficial because here an intimate bonding of super absorbing polymers and/or super absorbing polymer particles and the fibers or filaments is already formed, which is subsequently suitable to permanently activate the textile fabric and/or a fleece comprising the textile fabric.

There is a multitude of methods to form fleeces, and here particularly to form fleeces from nano-fibers and/or micro-fibers, which are also included in the generic term fleece. For example, it is considered advantageous when in the context with the textile fabric according to the invention the fleece is embodied as a fleece made from fibers randomly arranged, spun, and/or stacked. The application of a respective fleece-forming method depends on the later intended use of said fleece and/or the ultimate embodiment of the textile fabric comprising the fleece. Here, the application of the fleece made from randomly arranged fibers is particularly preferred because the super absorbing polymer can be integrated into the fleece with a particularly high level of homogeneity. In the production process for the fleece made from randomly arranged fibers the polymers used for the fiber production, provided in a liquid form, are preferably ejected from a nozzle and cooled in an air flow. By this air flow the forming filament and/or the fiber formed is transported to a conveyer belt embodied as a sieve and fixed via suctioning on this so-called sieve belt. Simultaneous to the ejection of the polymer from the spinning nozzle an impingement can occur of the air flow and/or the conveyer belt with the super absorbing polymer and/or with respective particles. They are interwoven and/or spun-in by the filaments, also reaching the sieve belt, to the fleece forming and thus fixed in their position. In order to ultimately determine the profile of features of the fleece formed, subsequently a needling process and/or a reinforcement of the fleece formed can occur, as already described above. During the production of a fleece in the form of a stacked fiber fleece the fibers are placed in a so-called carding to form a fleece. Here, the carding combines loose individual fibers to form a fibrous web, the fleece, and aligns them parallel in reference to each other. Here, too, the super absorbing activating means is integrated in the fleece in the same fashion. After the formation of the crude fleece reinforcement of the fleece can occur in the methods already described. The invention is not limited to the above-described methods to form fleeces, but it also relates to all fleeces that are produced in seemingly suitable methods and also extends to textile fabrics woven, knitted, or in another form connected from fibers or filaments. Here, of course, there is also the option that already activated fibers or filaments, i.e. already impinged with super absorbing polymers, are used for the formation of the fleeces and this way activate it in a super absorbing fashion.

Preferably a mechanical connection of super absorbing polymers and/or particles formed from the super absorbing polymer and the fibers or filaments of the fleece and/or the textile fabric formed from the fleece can be achieved such that the particles are held by the fibers or filaments in the textile fabric being placed cross-wise over top of each other and/or particularly spun into them. This embodiment of the textile fabric according to the invention also ensures a particularly lasting and durable, particularly wear and wash-resistant bonding between the super absorbing polymer and the fleece and/or the fibers or filaments of the fleece and thus the textile fabric. This bonding can also be improved, if applicable, by the additional, particularly simultaneous or subsequent impingement with an adhesive. In this context it is also considered particularly beneficial for the textile fabric to be provided for repeated use. Here, it is also beneficial for the textile fabric to be embodied washable, particularly machine washable or tolerating dry cleaning, and also withstands disinfecting or sterilizing treatments. These features of the textile fabric are implemented by the particularly lasting bond between the super absorbing polymer, which is implemented in the form of a coating by particles integrated during spinning, by super absorbing polymers or particles adhered to the fibers and/or the fleece, or the surface of the fleece. When using adhesives, it must be emphasized that they withstand several washing processes and/or disinfecting or sterilizing treatments of the textile fabric and cannot be dissolved from the textile fabric by the washing, cleaning, or disinfecting means and/or methods used, and/or by the temperature impingement during the washing or sterilization process.

In the interest of a particularly close bond of super absorbing polymer particles and fibers or filaments a structuring or coating of the surface of the particles and/or the fibers or filaments is considered particularly recommended. This coating and/or structuring of the surface can here be embodied such that the surface structuring or coating develops an adhesive effect. The structuring can be implemented into the respective surfaces by chemical or mechanical treatments. The surface structuring is here particularly embodied in the form of nano-structuring or nano-coating. The embodiment of the particles and/or the fibers or filaments with the above-mentioned structuring or coating of the surface is advantageous such that the bond between the fibers and filaments and thus the fleece and the super absorbing polymers and/or the particles formed therefrom can be performed without the additional use of adhesives or other adhesion-effecting substances, and also a wear of the structuring cannot occur or only to a limited extent during the washing or disinfecting and/or sterilization processes, thus the bond between the fibers and filaments and the super absorbing activation is embodied in a lasting and particularly durable and wear-resistant fashion.

One of the embodiments of the textile fabric according to the invention considered advantageous provides that at least one surface of the textile fabric is formed from a material different from the other textile fabric or from the same material, with the surface then showing features deviating from the other features of the textile fabric. It then proves beneficial for the surface of the textile fabric to be formed by a mechanical, thermal, and/or chemical post-processing and here particularly by a mechanical needling, for example by a treatment of the respective surface of the fleece with water jets or needle bars/rods. Using the embodiment of the surface described in the above preferred embodiment an exterior boundary of the textile fabric can be achieved, without here the application of additional material layers or coatings being required. The textile fabric is then entirely made from the above-described fleece, which had been subject to surface treatment. In this context it is also considered beneficial for the surface to be formed from a non-super absorbing activated fleece, a membrane, a film, a fabric and/or a fabric web or a coating, with here particularly the surface being connected to the remaining material of the textile fabric in a fixed or detachable fashion. There is also the option, here, for an above-described fleece to be coated additionally with another fleece not showing activation. Instead of a fleece, here also a membrane, a fabric, or a fabric web can be used, thus simultaneously another activation of the entire textile fabric occurs such that the membrane, the fabric, or the fabric web show a structure, for example allowing the evaporation of water vapors from the textile fabric, however not allowing the entry of water. The arrangement of such membranes, fabrics, or fabric webs on an exterior side of the textile fabric for example causes a water tight state at least at one side, without compromising the other features of the textile fabric. In addition to the arrangement of a membrane, a fabric, or a fabric web, according to the invention there is also the option to use a film as the surface for the textile fabric. This way, a complete seal of the surface from water entering or water vapors exiting is ensured so that during the evaporation of liquids stored in the super absorbing polymers a controlled and/or targeted removal of developing water vapors can be performed.

This embodiment of the textile fabric according to the invention allows its use under critical conditions with regards to aspects of contamination. The film used as the surface prevents any direct contact of the fleece and/or the interior of the textile web with the covered area to be cooled. The same effect is caused by a coating of the surface and/or an embodiment of the surface as a coating. By the suitable selection of the coating means additionally a further activation of the textile fabric and/or its surface can be performed, which will be discussed in greater detail in the following. It is considered another feature of the preferred further development of the textile fabric according to the invention that the surface is bonded with the other materials of the textile fabric in a fixed or detachably fashion. While a detachable bond of the surface and/or the surface-forming material with the other material of the textile fabric allows increased flexibility of the textile fabric, the fixed bond of surface and, for example, fleece material results in a considerably more compact design of the overall textile fabric and simultaneously prevents and/or aggravates damages of the textile fabric and/or any tearing or damaging of the surface. Another preferred embodiment of the invention provides that the surface is formed by the fibers or filaments melting with each other or melting together. Here, no additional layers are arranged at the textile fabric, but based on a finishing or processing of the surface a sealing of the textile fabric is created. Depending on the level of soiling, here an impermeable surface can also be formed. A particularly beneficial embodiment provides here that the melting together of the fibers or filaments to form the surface is performed in connection with needling. This way, not only a sealing of the textile fabric is performed, but the surface and/or sealing layer is additionally reinforced by said needling. Here, a treatment of the surface with water jets has the same effect as a needling. There is the option to first needle the layers of the fleece near the surface and then to subject them to a thermal treatment, with the fibers and/or the fibrous surfaces being partially melted and bonded in the liquefied state and/or after partial liquefaction or softening of the surfaces of the fibers.

Another exemplary embodiment of the invention provides that the surface is embodied permeably and shows pores for the penetration of liquids and/or gases, particularly comprising water, alcohol, alcohol/water mixtures, and/or vapors of water, alcohol, or water/alcohol-mixtures. By this embodiment of the surface the cooling effect of the textile fabric can be further improved, because the vapor developing during the evaporation of the liquid stored in the super absorbing polymers can be released from the textile fabric. The permeability of the surface with regards to liquid allows simultaneously a problem-free charging of the textile fabric by way of immersing or spraying with liquid. Due to the fact that the pore size is embodied smaller than the minimum diameter of the super absorbing particles perhaps used in the textile fabric, it is prevented that particles released from the bond, intended to be permanent, with the fibers or filaments and/or the fleece, can fall out of the textile fabric. This way, a permanent and consistent cooling performance of the textile fabric is ensured. As already mentioned, the surface, which can be formed as a membrane or film simultaneously prevents gel formation, caused by the dropping particles and developing when several particles which have collected to form a conglomerate contact liquids, can be sensed at the exterior, i.e. at the surface facing the user of the textile fabric.

It is considered recommended for the textile fabric to be compartmented. Said compartmenting can occur by way of quilting, sewing, adhesion, or welding of the surface of the textile fabric. Such a compartmenting of the textile fabric leads to an improved adaptability of the textile fabric to the surface respectively to be cooled. Additionally, it can be prevented that particles separating from the textile fabric and/or from the fleece or the fibers or filaments forming said fleece are distributed over the entire textile fabric and here form points or sections at which the particles collect and accumulate. This compartmenting of the textile fabric can also lead to a homogenous and primarily evenly distributed cooling over the entire textile fabric, even in case of separating particles. The quilting, sewing, or adhering of the textile fabric to implement this compartmenting can here occur subsequently, i.e. after the production of the textile fabric, for example also after the placement or arrangement of additional (cover) layers in or on the textile fabric. Simultaneously, there is also the option to provide compartmenting during the formation of the fleece and/or the finishing or processing of one or more surfaces of the textile fabric or fleece. In particular the welding of the surface to implement said compartmenting and/or to achieve a less permeable surface may be performed in a single processing step during a thermal treatment of the surface of the fleece and/or the surface of the textile fabric. During the compartmenting of the textile fabric, a fixation of the surface can occur, otherwise detachably connected to the textile fabric, which for example is formed by a membrane, a fabric web of a veil, a film, or the like, but also an additionally applied or connected, not super absorbing activated fleece or another suitable material, applied at the seams and/or welding spots to the textile fabric.

In order to create an option for using the textile fabric in a multitude of environmental conditions and simultaneously allowing to provide the textile fabric for a multitude of applications it is considered beneficial for at least one surface of the textile fabric to show an additional activation. Such an activation may be achieved, in addition to the potential chemical or physical finishes known from prior art in the field of textiles, by a finishing of the materials used to form the surface, particularly fleeces, membranes, fabrics, or fabric webs and films, as described in the following. The term finishing in the context of the present invention represents a processing measure of the source material of the fleece, its fibers, or filaments, and/or the substances, threads, films, or fibers forming the surface, in order to adjust and/or optimize the practical value and the material features of the finished material and/or the cover for the respectively intended purpose.

Furthermore, the textile fabric is also suitable for the use in fire fighting and/or in fire and heat protection, with here the flame-proof and/or fire-proof, spark resistant, and/or metal/ember resistant activation/equipment of the surface and/or the materials is suitable to prevent or retard a burning and/or damaging of the surface even when no residual liquid is preset in the super absorbing polymers and/or the textile fabric. The respectively activated textile fabrics are then also suitable for the use in heat-protective covers and occupational protective clothing, in which annealing or highly heated liquids must be handled, such as in melts and/or iron- or glass manufacturing. This also applies to fighting flames in fire fighting and as well as to prevent spreading fires.

The surface can additionally show a hydrophilic activation/equipment in order to this way improve and/or accelerate the charge of the cover and/or the textile fabric. This way, fabrics, webs, or materials designed, by their production or intended use for not absorbing liquids and/or water, can be activated for said purpose and/or retrofitted. Such equipment then allows the use of the original mechanical features of the materials with the simultaneous use of the textile fabric and/or the cover in the sense of the present invention. Rendering it hydrophilic can be performed for example in fabrics or substances used for firefighting as fire or heat shields, because the materials used here generally show no or only little water absorption capacities, however they can absorb liquids after respective retrofitting, store it, and conduct it further to the super absorbing activations.

In order to allow a particularly simple reuse and/or recycling of the textile fabric, at least one surface of the textile fabric comprises a self-cleaning activation/finishing. This self-cleaning activation/finishing can be performed for example by coating with nano-particles and/or by adding nano-particles to the source material. Additionally there is the option to activate/finish the surface for it to become dirt-repellant, with here all techniques can be used already known in prior art for the textile field in order to render the surfaces with a dirt-repellant activation, and/or to appropriately finish fabrics, threads, or fibers. Particularly when using the textile fabric for medical cooling or for other microbially critical applications, for example also in the food sector, it is recommended to coat and/or finish at least one surface of the textile fabric such that it becomes biocidal, antiviral, or antimicrobial. Such coatings/finishes can here additionally be applied on the surface of the textile fabric and/or integrated therein. However, there is also the option for the components of the textile fabric and here particularly the fleece to be activated/finished to be antimicrobial. In any case, the activation can occur by the additional impinging of the textile fabric, the fleece, or the fibers or filaments forming the fleece with appropriately activating/finishing substances. Here, for example the additional arrangement/application of nano-particles is possible as well as the interweaving or spinning of silver threads, which then develop the anti-microbial effect in the combination with the liquid inserted into the textile fabric. In the context of a biocidal coating there is the option to activate the textile fabric to become algaecidal, fungicidal, or herbicidal, in order to then use it as a cover. Additionally, there is the option for repellant, UV-blocking, and/or antistatic coatings and/or finishes the surface and/or the materials, substances, films, or membranes forming the surface.

In addition to the above-mentioned activations and/or finishes of the surface, the materials forming the surface and/or the textile fabric, here an additional finishing and/or application with substances can be performed, particularly advantageous for the use in cosmetic or medical applications. Such substances can represent, for example, skin care substances, such as products based on aloe vera, or other substances considered dermatologically beneficial. In addition to these substances there is the option of an additional application, equipment, or coating and/or moistening of the surface of the textile fabric and/or the materials forming the coating with substances supporting wound healing so that the textile fabric, which according to the invention can also be used as a wound covering, here shows additionally a wound healing effect.

When the finishing of the surface and/or the covering and/or the materials forming the textile fabric is performed chemically, by adding, applying, or incorporating appropriate substances adjusted to the respective finish, said finishing may be lost during use and/or after several cleaning processes and/or suffers loss of effectiveness. In order to renew and/or refresh the finishing it is provided to add refresher and/or renewal means or substances for the liquid used for the activation of the textile fabric in order to this way restore the finishing and/or create a respective finish.

The invention also includes a method to produce a textile fabric comprising the above-described embodiments. Here, the method according to the invention comprises the steps of providing fibers or filaments. This provision may occur in a spinning process, with here preferably fibers or filaments are formed by dry spinning, wet spinning, melt spinning, matrix spinning, or electro-spinning. In the spinning process a fleece is produced from the fibers or filaments yielded, which subsequently or during the production process serves to accept the super absorbing polymer. For this purpose, the method comprises the additional step of applying or inserting super absorbing polymer. According to the invention, this occurs in, on, or at the fibers or filaments and prior to, during, or after the provision of the fibers or filaments. Depending on the arrangement of the super absorbing polymer at, in, or on the fibers or filaments the bonding of the fibers or filaments with the super absorbing polymer occurs in another or simultaneous step of said process. Here, it may be provided on the one hand such that the particles are distributed loosely between the fibers stacked to form the fleece and by the fibers and/or filaments ultimately being fixed in the fleece. On the other hand, there is also the option that, when the super absorbing polymer represents an interlaced copolymer, first the precursor of the polymer is mixed with the fibers or filaments and then an interlacing of the precursor occurs to form the finished, super absorbing polymer. During the interlacing process, in which molecular chains are formed from the precursor of the polymer, then a fixing of the polymer occurs to the fibers or filaments and ultimately the activation of the textile fabric. As another step, the method according to the invention comprises the formation of a textile fabric developed from fibers or filaments and/or from the fleece formed from fibers or filaments.

In an advantageous further development of the method it is provided for the bonding of the fibers or filaments to the fleece and/or to the textile fabric occurring via a mechanical, chemical, or thermal connection. In a mechanical bonding the super absorbing polymer alone is given by the adhesion to the fibers or filaments and/or by the respectively tight packing of the fibers or filaments in the fleece. In a thermal bonding of fibers and/or filaments and super absorbing polymers a superficial melting of the fibers or filaments occurs so that here a softening or liquefaction of the fibrous material occurs and the super absorbing polymers are ultimately melted to the fibers or filaments. After the re-hardening of the fibers the super absorbing polymers then remain bonded to the fiber. During a chemical bonding between fibers or filaments and the super absorbing polymer the additional impingement of the fibers or filaments and/or the fleece or textile fabric formed therefrom occurs via an adhesion or interlacing means. When an impingement occurs with an adhesive, an additional substance is introduced into the textile fabric, which then facilitates the adhesion between the fibers or filaments and/or the fleece or the textile fabric and the super absorbing polymers. When an interlacing means is used as the chemical bonding agent it only acts upon the super absorbing polymers and causes them to interlace and in the process thereof their bonding to the fibers or filaments of the fleece and/or the textile fabric. Additionally, by chemically impinging the fibers or filaments and/or the fleece or textile fabric a superficial partial melting of the fibers or filaments can also be achieved, which are then capable to enter into a permanent bonding with the super absorbing polymers for example provided in form of particles. This lasting bond occurs after the drying and/or neutralization of the chemical substance softening the fibers and/or "melting" them. In addition to bonding or interlacing super absorbing polymers and fibers or filaments and/or fleece or textile fabric, the bonding of the fibers or filaments themselves may also occur in one processing step. Here, too, it is possible to cause the respective bonding and thus the reinforcement and/or compacting of the fleece by chemical, mechanical, or thermal influences. Here, the bonding of the fibers or filaments may occur by way of needling. Equally effective for the bonding of fibers or filaments is a water jet treatment of the crude fleece, in which similar to needling a reinforcement and further bonding of the fibers or filaments is performed. In chemical bonding, an impingement of the crude fleece occurs with an adhesive and/or with a substance attacking and softening the jacket of the fibers so that the fibers or filaments are connected to each other at the respective intersections and adhere to each other. The thermal bonding method has already been discussed for the formation of the surface of the finished fleece. Here, the impinging of fibers or filaments occurs with a warmed or heated gas flow or via steam, which leads to at least the jacket of the fibers to melt or soften. Such softened or melted fibers are glued together after a subsequent pressurization of the crude fleece and then during the cooling of the fleece curing occurs of the bonded fibrous structure and a lasting connection of the fibers therein. Another preferred embodiment of the method provides that the fibers or filaments are formed by dry spinning, wet spinning, melt spinning, matrix spinning, or electro-spinning and a bonding occurs of fibers or filaments and/or a source material for the fibers or filaments and the super absorbing polymer prior, during, or after the spinning process. Here, the fibers or filaments are formed from a polymer or polymer mixture, which is provided prior to spinning in a liquefied state. The polymer solution can then be mixed with the super absorbing polymer, which for example is provided in the form of particles or also as a solution, and in the subsequent spinning process spun jointly with the fiber or filament polymer. The super absorbing polymer is then integrated and fixed to the structure of the fibers or filaments and thus activates them to become super absorbing. In this process, no additional impinging with a super absorbing activation means is required for the fleece formed from fibers or filaments and/or the textile fabric comprising it. Of course, this can additionally be implemented in order to further activate the ultimately formed textile fabric. In addition to introducing the super absorbing polymer as an additive for the source material of the fibers or filaments, of course there is the option for the fibers or filaments to be formed entirely from said super absorbing polymer. This in turn is then also used in the above-mentioned spinning process, with here fibers or filaments being formed. Of course it is also possible that the super absorbing polymer is used together with another carrier substance, for example when a super absorbing polymer is used which cannot be processed by spinning processes. In addition to a simultaneous or almost simultaneous impingement of the fibers or filaments with the super absorbing polymer and/or another super absorbing activation means there is the option to provide a processing step in which after the formation of the textile fabric the super absorbing polymer is applied thereupon. Here, the above-mentioned option comprises a chemical interlacing of the super absorbing polymer and the fixation in the textile fabric connected thereto. Additionally, of course a mechanical bonding of the super absorbing polymer can occur with the textile fabric, for example when the super absorbing polymers are provided in the form of particles arranged between two fleeces which show no super absorbing activation. Here, too, first a precursor substance of the super absorbing polymer can be applied on the textile fabric and then, with a chemical interlacing means added, the ultimate super absorbing polymer being formed by way of interlacing after being inserted into the textile fabric. It is considered beneficial for the process when the super absorbing polymer is present in the form of particles. The particle shaped impingement of the textile fabric allows a particularly precise adjustment of the amount of polymer present and/or ultimately bonded in the textile fabric.

Another aspect of the invention comprises a cover, which includes two or more layers and here at least one textile layer formed from a textile fabric, as described above.

This cover may be formed as layers, e.g., an exterior or interior skin for example made from a planar material with at least one textile fabric being located there between. The layers of the cover are therefore provided in addition to the actual surfaces of the textile fabric and cover said textile fabric. Of course, there is also the option for the exterior or interior skin of the cover and/or the layers forming said exterior or interior skin resting planar on the textile fabric and thus directly contacting the surfaces of the textile fabric, as for example provided in a preferred further development of the cover according to the invention.

It has proven beneficial, also with regards to the charge of the textile fabric with a liquid, when the layer and/or the layers is/are formed from a woven or textile material.

Furthermore, there is the option to form the layer(s) as membrane(s) or film(s). This way, another functionality of the cover can be achieved, when for example via the layers encasing or accepting the textile fabric another function of the cover is achieved. For example, when the layer is embodied as a climate membrane here, even if the textile fabric is not used for cooling purposes, yet still an emission of water vapors can occur without here liquids entering from the outside into the cover because the membrane performs the respective function. The embodiment of at least one layer as a liquid-impermeable film, for example, allows the unilateral shielding of the cover against any liquids inserted into the cover, for example, to activate the textile fabric.

Additionally, there is the option to form the layer from a combination of one or more fabric webs, perhaps embodied in a sandwich structure, and one or more membranes or films. The layer may also comprise a micro-fiber material, which provides the advantage that here a rapid superficial drying of the cover is given because the liquid applied is quickly guided to the textile fabrics provided in the cover. The above-mentioned materials for the embodiment of the layer and/or the layers also provide for the use of fabric webs or textiles comprising metal fibers, functional fibers, such as coconut fibers, carbon or mineral fibers, of natural or artificial origin. For example, the use of coconut fibers is particularly advantageous because these fibers are very elastic, strong, and long lasting. In addition to high abrasion resistance these fibers are also resistant to fungi and bacterial infections and can withstand extended impingement with moisture without disintegrating. Another advantage of the use of coconut fibers is given in their insulating, noise-suppressing, antistatic, and hardly inflammatory features, so that covers comprising respective fibers and/or layers of covers are suitable for the use in moist environments and additionally ensure other functions of the cover by their nature. Similar benefits apply for bamboo fibers as well as other innovative functional fibers.

The advantage of the use of carbon fibers is their long life with simultaneously a low weight and high stiffness. By the use of mineral fibers of different embodiments additional functionalities can be achieved for the cover, which therefore further increase the range of application for the cover in cooperation with the textile fabric according to the invention.

When metal fibers are used in the cover, the advantage develops that due to the thermal conductivity respectively achievable here by the selection of the metal, said thermal conductivity of the cover can be adjusted and thus the cooling performance of the respective cover can be defined or subjectively enhanced.

The cover according to the invention is also suitable for covering vehicles, ships, airplanes, equipment or machinery. Here, in addition to a cooling effect, the infrared-visibility of the devices, machines, vehicles, airplanes, or ships heated during operation, can be reduced or even eliminated during the operation of the respective vehicles, devices or machines. This way, the thermal radiation of the respective vehicles, airplanes, ships, equipment or machines or even buildings can be prevented so that they cannot be detected any longer by appropriate detection devices (for example thermal imaging cameras or the like). In the mobile application of respective covers, for example on vehicles, at ships, airplanes or trains, they become almost invisible for the respective detection devices and/or their shape is appropriately camouflaged.

A preferred embodiment of the invention provides that either the surface of the textile fabric or at least one layer of the cover comprises a finish which shields the covered or encased object from electromagnetic radiation or absorbs such radiation. This way, on the one hand, an improved protection of the respectively covered objects, vehicles, equipment, devices, but also body parts or the like is achieved from the impingement of electromagnetic radiation, on the other hand the covered object, the encased vehicle, the respectively covered machine, or an appropriately encased building becomes invisible for another segment of the electromagnetic spectrum and is therefore no longer detectable or traceable with respective detection devices.

The respective equipment of the cover is for example applied to the exterior of the layer or integrated therein. The embodiment of the respective equipment therefore depends on the respective purpose for use, i.e. if here only a shielding shall be achieved from electromagnetic radiation or if the electromagnetic radiation must be absorbed entirely.

In another aspect of the invention the textile fabric, provided in the cover, comprises one or more membranes, which either cover the textile fabric and thus define the surface or perhaps functionalize it appropriately or which in addition to the fleece are provided themselves arranged within the textile fabric or arranged at said fleece or even in said fleece itself. This leads to a compartmentalization of the fleece and simultaneously an improved control of the release of liquid and/or the emission of water vapors but also improving and controlling the penetration of liquid and/or its distribution in the textile fabric.

The cover is advantageously embodied as a textile material, functional textile, functional cooling element or pad, a piece of clothing, clothing accessory, suspenders, protective clothing, a liner arranged or to be arranged fixed or detachably to a piece of clothing, such as particularly a jacket, a suit, trousers, an apron, an overall, or the like, a tarp, a blanket, a ceiling or roof structure, medical product, surgery blanket, pulse cooler, scarf, cooling tape, cooler, bandage, foot or joint bandage, orthotics, facial or eye mask, stockings, pantyhose, head covering, helmet, shoe or boot, a cover, particularly for buildings, vehicles, airplanes, ships, machines, equipment, surfaces or floors, as cover tarp and/or covering protective tarp, as awning, tent material, sun roof, or as equipment for protection from high temperatures, as a bag, tote, blood or blood-product bag, as a bag for organ transport, as a bottle or ampoule cooler, for the protection of biological and/or human components and substances, as well as pharmaceutical effective agents and products from excessive heating and from high temperatures, as a backpack or another sport or outdoor product showing a cooling effect, for example as a sports jersey, sports attire, underwear. Additionally there is the option of an embodiment as a storage, transportation protector, or animal cooling product, particularly for cooling agricultural livestock such as cows, or as cooling vests for pets, such as dogs or cats as well as cooling blankets and/or bandages for horses, dogs, or cats as well as all other embodiments that seem suitable in this context. When the cover is embodied as a cooling functional element, here it is also included that the functional element is suitable for insertion into the pocket or several sections and/or parts or a piece of clothing, in order to here perhaps also be used for cooling, if applicable.

It is particularly advantageous to use the cover provided with the textile fabric for medical cooling. Said cooling is usually performed by ice accumulators, ice-cooled gel cushions, etc. However, specialists and physiotherapists warn about localized hypothermia, caused by ice due to the constriction of vessels, particularly at temperatures below 10° C.-15° C. Additionally, cooling is effective for a short period of time only, wetness develops by water condensing, and the materials are hard and heavy. Therefore it is beneficial to provide alternatives to conventional ice applications in order to faster relieve the suffering of human patients and animals (such as horses) and to prevent adverse effects, as the ones arising from ice bags.

The textile fabric provided in the cover can here be arranged fixed in the cover and/or at or in the actual product or implemented as a cooling functional element, for example entirely separate from the cover. Additionally, there is also the option to insert the cooling functional elements into a piece of clothing or provide it as a detachable or fixed liner. Here, the piece of clothing comprises suitable pockets or fastening points. The charged and activated functional element or the liner is here inserted, as needed, in said pocket and/or arranged at the piece of clothing and/or the object and cools here in a proven manner either punctually or over a wider area the body or object carrying the product. Of course, there is also the option to provide bandages adjusted to the body part and entirely or partially provided with cooling elements, such as orthotics, like gloves, foot socks or the like, which are equipped with the functional cooling element formed from the cover according to the invention. A respectively activated piece of clothing and/or cover is suitable, for example, also by cooling in case of cardiovascular complaints.

Based on heat effects, primarily in older people with cardiovascular deficiencies or pets and/or agricultural livestock, such as older dogs, horses, cats, cows, etc. with cardiovascular deficiencies rapid and simple cooling at high temperatures is particularly important. In the summer months and in countries with hot climates people and animals dying from heat exhaustion should not become the rule. Particularly in this field, temperature control of the body is useful and can be performed via cooling pieces of clothing, head coverings, and accessories. Due to already weakened cardiovascular systems the appropriately embodied covers according to the invention are suitable, because depending on their embodiment they show a low weight and no icy temperatures, but physiologically cool temperatures, i.e. above 10° C.-15° C. When used at the body, for example as a piece of clothing, here no water droplets or gel-like residue forms at the clothing, which then could reach the surface of the body of the wearer. Here, the invention also includes textile covers, particularly miscellaneous textile products, such as pieces of clothing, but also underwear, which is directly worn on the skin and thus develops its cooling effect directly, as well as sports attire and the like. Particularly in the field of sports, as well as in occupational protective clothing, the body saves energy, because the cooling product supports the thermal regulation of the body and provides relief. This increases the performance during work but also in sports. In trials, here 5% to 10% increase in performance was found.

In the field of occupational safety the relief for the cardiovascular and the metabolic system of the wearer must be added, which leads to lower out times, accidents, and sick days and overall a longer work life.

In the medical field it is provided that the cover according to the invention is used for example as a foot or joint bandage (e.g., knee, hip, shoulder, hand, or arm joint) or also as a stocking or pantyhose. In the field or surgery the cover according to the invention can also be used in various ways. In addition to a surgery blanket, it is also possible to provide respective face masks or eye masks and for example in the facial areas for respective surgeries, such as plastic surgery or reconstructive surgery, it can provide a fast but not excessively cold and lastingly operational cooling.

Furthermore, the invention includes pulse coolers, scarves, cooling tapes, coolers, or other objects in which a respectively cooling effect is advantageous.

Another field of application of the invention is particularly given in the use of the invention implemented in a cover made from a textile object for the use as a sun roof, awning, and/or tent material.

Additionally, the utilization according to the invention is also beneficial for head coverings, such as helmets and the like, with both occupational protective helmets (firemen's helmet) as well as recreational helmets being used, such as motorcycle helmets or bicycle helmets, or fencing helmets in the field of sports, which experience a considerable improvement by the use of the invention.

Furthermore, using the cover according to the invention and/or its respective embodiment cooling can also be performed in cases of multiple sclerosis and other neurological diseases and injuries. The heat sensitivity of approx. 80% of patients suffering from multiple sclerosis (MS), characterized by the Uhthoff phenomenon, leads at higher temperatures to more severe symptoms and disease progression as well as fatigue. Additionally, paralyzed persons, patients suffering from Parkinson's disease, and other neurological diseases tend to have heat sensitivity and fatigue syndromes. These symptoms can be reversed by cooling the body, and are even prevented by body cooling. Due to the fact that these patients usually are already limited with regards to their mobility, but in spite thereof participate in public life, it is recommended here to provide the cover according to the invention as a cooling piece of clothing, which is embodied lightly and still provides a lasting cooling effect.

When using the cover as a piece of clothing, as a blanket, or covering the lasting arrangement of the super absorbing polymers in the textile fabric and/or the bond of the polymer with the fibers or filaments of the fleece are particularly important. By the embodiment of the textile fabric according to the invention and/or the cover during application no particles or other super absorbing activation means become loose from the piece of clothing, the blanket, or cover or the like, which otherwise perhaps might allow the formation of moisture at the surface facing the body. Here, it must be considered another advantage of the embodiment of the invention that it can be used quickly and particularly easily transported in the uncharged state. The cover and/or the textile fabric arranged therein can then be charged on site and/or as needed and develop its cooling function.

Particularly when used as a medical product, the antimicrobial, antiviral, or biocidal impingement of at least the surface of the textile fabric and/or the cover is particularly important, in order to here largely reduce the risk of contamination or infections. Additionally, an embodiment of the cover that is washable and/or can be disinfected or sterilized is recommended, at least the upper and/or exterior surfaces.

In this context, it must be mentioned, of course, that antimicrobial, antiviral, or biocidal impingement and/or effect of the textile fabric and/or individual components of the textile fabric (fleece, SAP-activation, etc.) can be used not only for medical products but also for applications that are outside the classical medical field, such as the areas of sport, occupation and the like.

The antimicrobial, antiviral, or biocidal impingement and/or activation and the sterile or disinfecting effect resulting therefrom occurs here, for example, directly at the fiber, before it is processed into a fleece. Alternatively it is possible to arrange this impingement and/or activation on the planar fleece, namely both prior as well as after the arrangement of the super absorber in the fleece. Here, it is also possible for the entire finished textile fabric to be treated with an antimicrobial, antiviral, or biocidal impingement.

Finally, it is also possible that the cover fabric, and/or the (cover) layers forming the exterior or interior skin of the cover between which the textile fabric is installed shows antimicrobial, antiviral, or biocidal features and/or impingement.

The cover and/or its respective embodiment as a blanket, cover, piece of clothing, etc. is also suitable for cooling in case of heart attack or stroke, of course. It has been shown in numerous studies and publications that the survival rate of patients with a heart attack or stroke, particularly in case of cardiac arrest, is considerably higher and subsequent symptoms due to said infarct or stroke are milder if the body of the patient is cooled below the normal body temperature. This is also the approach of stationary apparatuses. The cover according to the invention provides a solution here, which can already be used during the ride to the hospital and/or during the transportation in the hospital and allows for the cooling process to be upheld. Here, due to the embodiment of the cover according to the invention disadvantages are avoided, such as moisture, uncontrolled ice cold temperature, heavy weight, etc.

The cover according to the invention is also optimally suited for other medical fields. The good suitability is here defined by the cooling temperature available, which ultimately depends on the liquid of the charge as well as the potentially very long lasting cooling feature. Here, it has been found that excessive cooling, i.e. cooling with an excessively low temperature, leads to adverse effects. For example, a respective disinfecting and/or sterile cover can also be used for blunt injuries, surgeries, but also for swelling, contusions, and injuries caused by injections. The range of application therefore also includes surgery, as well as orthopedics and plastic surgery. Particularly in the latter named surgical field a careful but long lasting cooling effect is advantageous.

Another field of application of the cover according to the invention is cooling in sports, in recreation, and at work. Due to the high energy required for the thermal regulation of the body, humans and animals and here particularly laborers and athletes suffer considerable loss in performance beginning already at 18° C., which is further increased by higher exterior temperatures. The use of cooling prior and after sports, during exercise, and in resting phases can save energy which leads to a considerably higher performance. Cooling at hot work environments increases concentration and performance and prevents health detriments. Syndromes of exhaustion can be prevented. Here, too, a simple, clean, dry, and wear-resistant cooling product in the form of the cover according to the invention is useful, which operates both with as well as without preliminary cooling over an extended period of time. Here, the effect is considered positive that the additional cooling from evaporation during preliminary cooling results in synergy effects, which is sufficient for providing additional cooling effects of a temperature reduced by up to −2° C. Additionally, the cooling period is considerably extended, which considerably increases the range of application, primarily at high humidity.

Another field of application for the cover according to the invention and/or one of its numerous embodiments is the use for cooling objects and the environment. Cooling is important and partially mandatory at hot work stations, (e.g., in the proximity of machines, equipment, kilns, melts, etc.), in the proximity of fire (e.g., during firefighting in houses or forest fires), or in countries with a hot climate or in summer (e.g., under awnings, in tents, or under roofs) as well as to achieve and/or maintain a certain temperature of products (e.g., foods, blood bottles, drugs, ampoules, bottles, etc.) and during the transportation and in logistics chains. Due to the fact that a continuation of other cooling cycles is not always possible and partially excessively low temperatures occur here, and the respective continuation is also connected to high costs, here an energy-independent cooling system like the one provided by the cover according to the invention is particularly advantageous.

Of course, there are other cooling applications, such as in the context with premature births, in chemo and radiation therapy, in diseases of the central nervous system and metabolism, in hyperthermia, burn injuries, laborers under hot conditions, and other situations, which cannot be discussed in greater detail here, which however are included just as well. The cover according to the invention in all its embodiments is suitable however for all cases of cooling, targeting to reduce the influence of the environmental temperature on a body or object to such an extent that here no lasting damages must be feared. The cover according to the invention and/or the cooling system provided here offers numerous advantages, because it relates to a simple, quickly applicable, and primarily superficially dry and device-independent cooling system, which additionally shows a long lasting cooling performance and can be combined with other cooling systems, if applicable.

In order to ensure an application of the cover according to the invention as wide range as possible it is considered advantageous for the cover to be machine washable. Additionally, dry cleaning, sterilization, or disinfection of the cover can be performed beneficially. In addition to the above-mentioned cooling effect the cover beneficially also provides an air-conditioning effect. An air-conditioning effect is considered that the cover according to the invention cools not in an uncontrolled fashion but rather is suitable to maintain a constant level for the temperature status of a person or object covered. In addition to this air-conditioning effect, the cover also provides the additional positive effect upon the climate because cooling by using the cover according to the invention is $CO_2$-neutral and thus it can occur environmentally friendly. Here, it is beneficial for the cover to be cooled only after or by way of charging with liquid, particularly water, or a mixture with water content. Another improvement and/or extension of the cooling performance is achieved when the cover and/or the textile fabric is charged with a previously cooled liquid and here for example with a pre-cooled saline solution. This means that in the uncharged and/or not with liquid or moisture charged state the cover shows only light weight. Depending on the embodiment of the textile fabric according to the invention here additionally first a certain insulation and thus heating effect may be given by the cover. The cover according to the invention therefore shows dual benefits. This is particularly advantageous in medical applications, because using the cover according to the invention can be provided both as an insulating cover as well as a cooling cover, as needed. By suitably coating the surface of the cover, for example with a reflective layer, the insulating performance can be improved. Simultaneously the reflective layer extends the cooling period in case of cooling application, because the heating by thermal radiation is reduced. Only after being charged with moisture the cover develops a cooling effect by way of evaporating the charged liquid and/or due to the temperature of the liquid, and thus cools the body or object covered and/or holds its temperature constant to a certain extent. Another embodiment of the cover according to the invention provides that it is not exclusively used to cool after being charged with liquid but rather it is provided to preliminarily cool the cover in addition to the evaporation-related cooling in the charged state. Here, the above-discussed further cooling effect, in addition to the cooling by evaporation, is caused by the medium filled into the cover being pre-cooled or by pre-cooling the product after it was charged with liquid.

Additionally, it is provided according to the invention that the cover is charged with a liquid, formed from a mixture of alcohol and water. This charge with a mixture of alcohol and water causes that immediately after the charge an evaporation of alcohol and the reduction of the temperature of the cover connected thereto occurs due to the heat being removed during evaporation. After and/or simultaneously to the alcohol evaporating, additionally evaporation of the water included in the mixture occurs, creating a long lasting cooling effect in the cover. For an optimal cooling, it is considered particularly beneficial when the mixture includes alcohol ranging from 1 to 70% by volume, preferably from 5 to 50% by volume, particularly however from 10 to 30% by volume and water from 30 to 99%. Depending on the speed of cooling required from the cover, the alcohol portion in the mixture may vary according to the above-stated values and/or the range of these values. Therefore it is possible to adjust the cooling to the respective environmental conditions and/or exterior temperatures present when the cover is used and/or to adjust the cooling performance to said conditions or the specifications of the user.

The alcohol used in the mixture is beneficially selected from a group comprising ethanol, isopropanol, or mixtures of these alcohols. The use of ethanol and isopropanol is considered particularly suitable since the use in humans and animals is considered harmless.

In order to further improve the cooling performance or to achieve respective additional effects of the mixture used it is considered advantageous for the alcohol-water mixture to comprise adjuvants mixed in. Suitable adjuvants here are particular ethereal oils or fragrances (natural or artificial), which on the one hand result in an additional cooling, for example upon application on the skin, or during evaporation from a mixture filled in the cover and/or from a textile fabric arranged in the cover and particularly developing an aromatic effect experienced as being pleasant or operating as a repellant. The ethereal oils used preferably represent menthol or camphor, because here the respective cooling effect upon application of said substances on human skin is known and can be used for an additional cooling effect. In addition to aromatic or cooling effects, such adjuvants can also be added, which provide a repulsive effect for example upon insects or ticks and additionally protect the user of the cover from insect stings or tick bites. In addition to the use of menthol and camphor, here additional natural ethereal oils are possible, for example made from in cloves or aromatic sweet grasses. Artificial repellants, such as Icaridin or aromatics may also be used.

In order to prevent that the alcohol-water mixture is abused it is recommended to add a denaturant as an adjuvant. Regardless of the type of adjuvant used, it is provided according to the invention that its portion ranges from 0.1 to 5% by volume in the overall mixture.

In particular with regards to the use of the cover in the medical field, sterility is of particular importance. It is therefore considered advantageous and beneficial if the water used in the mixture is selected from a group comprising distilled water, demineralized water, or ultrapure water.

Depending on the hygiene and sterility requirements the respective specialist then selects the appropriate mixture to be added to the water component. If no higher requirements have to be met, tap water or mineral water may also be used. With regards to the alcohol used, of course there is also the option to use respective levels of purity (technical, for synthesis, pure, ultrapure, for analysis), which in turn also depends on the intended application and the given environment.

In a beneficial embodiment of the cover according to the invention it is provided that the mixture of alcohol and water and/or the mixture of alcohol and additives are provided as concentrates and only prior to charging the cover they are diluted with water to obtain the ultimate concentration. For example, the concentrate may be provided in the form of ampoules or particularly space-saving bottles, accompanying the cover for a later application as needed. Therefore, the user is given the option to charge the cover with water only or alternatively with a mixture of alcohol and water and/or with an adjuvant, with the latter charge and/or the respective means for the charge depending on the respective purpose for use and/or the requirements for the cooling performance of the cover.

Besides adding ethereal oils, fragrances (natural or artificial) or denaturants as adjuvants, the mixture may alternatively or additionally also comprise a component of biocides, fungicides, virucides, antimicrobial or antibiotic substances. Here too it is provided according to the invention that the additives in the mixture amount to a portion ranging from 0.1 to 5% by volume. By the above-mentioned substances on the one hand a conserving effect is yielded, and on the other hand it is prevented that a colonization of the cover occurs with organism, such as fungi or bacteria. This way, the cover is suitable for purposes of elevated requirements with regards to the hygiene of the product and additionally it can be achieved that during evaporation and the cooling use of the cover additionally a release of the respective substances occurs, which for example can be connected to a curing effect. For example it is recommended to add antibiotic substances for the use of the cover as a wound covering. The antimicrobial activation and/or finishing of the cover is primarily useful when the cover is used for cooling purposes for example in the food sector. Here, for example, relatively harmless silver solutions may also be used, particularly micro-silver or nano-silver. The addition of skin-care products is also possible, for example based on aloe vera or other dermatologically recommended substances. Means to support the wound healing are also suitable as additives.

The charging of the cover with a mixture is not limited to a mixture of alcohol and water and/or the other adjuvants described above in this context. Rather, here a mixture of water and other substances may be provided, which reconstitutes, refreshes, or generally creates the finishing of the cover and/or the textile fabric, because after several washing and/or cleaning processes such finishing of the surface and/or the cover weakens. The use of a mixture of water and a means restoring and/or refreshing the finishing and/or the respective substance can therefore be used during the charging simultaneously to renew or refresh the finish. To the extent chemically compatible, the respective refreshing means for the finishing may also be added to the mixture of alcohol and water. This way, for example the option is given to offer a multitude of differently composed mixtures allowing the user to select mixtures for the respective application in order to perform an activation of the cooling features and simultaneously a respective activation or specialization of the cover for a certain field of application. It is possible, for example, that the liquid used for the activation comprises a portion of water, via which the cooling performance is ensured and/or activated and additionally comprises an alcohol portion, which causes an accelerated cooling with the textile fabric and/or the cover and additional substances are added to the mixture, for example biocidal substances. Additionally or alternatively, a renewing or refreshing substance for the finishing may be added to the cover and/or the textile fabric, which is then applied to and/or inserted together with the activating liquid for the super absorbing portions to the material and/or the fabric and here appropriately refreshes and renews the finish. Such a liquid for renewal or refreshing the finishing can renew, refresh, or restore for example the resistance to sparks, the resistance to splashing metal and/or embers, and/or the fire resistance or the hydrophilic feature of the fabric, the surface, and/or the textile fabric.

An advantageous further embodiment of the invention provides that the cover is stored or transported in a fixed installed or mobile cooling container prior to or after the respective preliminary cooling. This embodiment of the invention is particularly suited for medical cooling in the above-mentioned cases and in emergency medicine. Here, e.g., a cooling blanket already charged with water and sterilized, vacuum welded in a plastic film, can be provided ready-to-use in the ambulance or rescue vehicle.

Additionally there is the option, for example in case of fires, to embody the cover as a covering tarp for objects or entire buildings and to transport it in respective boxes or other containers to the location of the fire. The cover then shows a dual effect, firstly the pre-cooled cover leads to a reduction in temperature in the proximity of the core of the fire and/or the covered object. When this effect is consumed by the continued impinging with heat, cooling occurs by the evaporation of the liquid provided in the cover. The duration of use of the cover is here significantly increased and the cooling effect additionally improved. In case of large tarps the fire can be reduced and prevented from moving to adjacent areas, objects, buildings, etc. The cover is further improved by impingement or impregnation with a fire-retarding substance. This increases the fire retardation and extends the time available for firefighting.

Another advantageous embodiment of the invention provides that the cover is used in a combination with cold air or in a refrigerator. By this measure and/or this use the cooling performance of the cover can be further improved and the cooling effect further extended. Here, the cover is particularly suitable for the treatment of inflammatory diseases in the medical field. Additionally, this embodiment of the invention provides that the cover is used in the context with food or other substances requiring cooling, such as medicine or temperature sensitive chemicals.

The cover according to the invention comprises two or more layers, as already explained. In this context it has proven advantageous for at least a portion of the cover and/or at least one layer to be formed from a fire or flame resistant, liquid metal repelling material, resistant to the impingement with liquid metal, water tight, self-cleaning, dirt repellant, antimicrobial, and/or biocidal material, or to comprise a material showing a rubber-like consistency. Furthermore, there is the option that at least one layer or one part of the cover comprises a fire or flame resistant coating, activation, or finish, resistant to liquid metal or repelling it, water tight, self-cleaning, dirt-repellant, biocidal, antiviral, antimicrobial, hydrophilizing or rubber like. The coating may be formed upon completion of the cover and/or after the arrangement of the respective layers at the textile fabric. Furthermore, it is possible that the layer and/or the layer material or a material encasing the textile fabric is provided with a respective activation, coating, or finishing and said material is only subsequently provided with the super absorbing activated component and/or bonded to the textile fabric of the cover. The respective activation, coating, or finishing can be applied at the cover and/or at least one of the layers by way of brushing, spraying, injecting, or immersion. If the coating represents a flame or fire retarding, biocidal, antimicrobial, or antiviral activation, respective substances or particularly impinged fibers may already be inserted into the textile fabric, the fleece, and/or the other materials forming the layer or the cover during their production or subsequently. Activation then occurs, if applicable, only in the context of being impinged with moisture. For a self-cleaning or dirt-repellant activation/finishing a direct treatment of the surface of the cover and/or at least one layer is recommended because regularly only this comes into contact with dirt or other contaminants. The respectively activated or coated layers or parts of the cover then, due to their activation, protect the remainder of the cover from dirt and contaminants and here particularly the super absorbing activated textile fabric provided in the cover.

In addition to the above-mentioned layer, using a respective treatment of the cover, hydrophilization can also be performed of certain fabrics, normally not allowing the absorption of water or liquids. After a respective hydrophilic finishing of respective materials or fabrics, then the absorption and/or the entering of liquid into the cover can also occur via this fabric, so that here an activation of the super absorbing activated textile fabric can occur, while the mechanical or other particular chemical features of the originally not hydrophilic fabric or material and a suitability for the respective purpose, for example the protection from fire, sparks, and strong impingement with heat remains.

An advantageous further development of the cover provides that channels are provided in one or more layers for ventilation or for distributing liquids. An appropriate embodiment is here particularly advantageous when the layer itself and/or the cover comprises a water tight or rubber-like coating and/or is made from a water tight or rubber-like material, which generally renders it impossible for water and/or liquids to enter. Here, the channels in the layers can conduct the liquid into the textile fabric using the capillary affect and here ensure the even distribution of the liquid, so that a homogenous cooling effect develops. Similarly, after the charge of the textile fabric and/or after activation of the cover by charging with liquid the channels serve to remove the water vapor forming during the evaporation from the cover and/or the textile fabric in order to maintain the cooling effect. It is considered beneficial for the channels to be embodied such that they can be closed manually, in order to allow a certain control upon the flow of liquids introduced into the textile fabric. Additionally, of course, it is also possible for the channels to be embodied automatically closing in order for an optional self-regulating impingement and/or introduction of liquid into the textile fabric. The automatic closure can occur for example when a certain temperature or moisture range has been exceeded or fallen short.

In this context it is considered beneficial if the absorption or release of liquid occurs via micro-pumps and/or when an osmotic absorption and/or release of liquid occurs. The use of micro-pumps ensures an even distribution of the liquid and/or its homogenous release to the cover and/or the textile fabric. Additionally, when it is considered recommended, a reservoir may be provided in the cover, particularly embodied as a tub, canister, or bottle or the like, serving to accept or release liquids. This reservoir may be connected to the micro-pumps so that they then remove liquid from said reservoir and distribute it in the cover and/or the textile fabric arranged therein. The removal of liquid from the cover and/or the textile fabric can also occur by micro-pumps. Additionally or alternatively a hose system may be provided, allocated to the textile fabric or the cover, and connected to the reservoir. Via said hose system, in cooperation with the micro-pumps or based on an osmotic difference forming, the liquid can be distributed in the cover and/or the textile fabric. Here, too, an even distribution of liquids develops, which results in a homogenous cooling effect.

The osmotic effect or the micro-pumps also allow a rapid emptying of the cover, for example when it is used to cover machines or buildings.

Thus, the micro-pumps not only serve to absorb but also to release liquids, as does the osmotic effect used for the absorption as well as release of liquids.

The textile fabric is advantageously arranged fixed at or in the cover. A connection between the textile fabric and the cover can here occur by connection means, such as gluing, welding, or sewing. In addition to a fixed connection of the textile fabric at or in the cover there is the option for the textile fabric to be arranged detachably in the cover. Here, it is then recommended to connect the textile fabric by insertion into a pocket provided in the cover. In addition to the arrangement of respective pockets, there is also the option to connect a textile fabric to the appropriately embodied cover, via buttons, a connection using a zipper, Velcro, or other detachable connection means.

The other connection means include, in particular push buttons, snaps, plug connections, clips, connection means using belts or straps, clamps, and the like. This detachable connection between the textile fabric and the cover is advantageous in allowing a flexible arrangement of the textile fabric and thus a flexible embodiment of the cooling and its execution. For example there is the option to cool only certain regions of the body of an athlete by inserting or arranging the textile fabric accordingly. The same applies of course in the context with the cooling of objects or animals, such as cooling patients. The arrangement of detachable cooling elements and/or textile fabrics causing the cooling effect as needed is therefore possible.

Furthermore, the invention provides a cooling system particularly suited for the use within the scope of a medically necessary, controlled, and monitored cooling of humans and animals, and a cover as described above. The monitoring can be useful not only in the medical field, but also in sports or occupational safety, in order to monitor the performance of the respective persons, e.g. The same applies for sensitive machines, equipment, airplanes, vehicles, ships, or other objects, if their temperature monitoring is useful and necessary. The medical cooling is here performed by physical evaporation of the water and/or another liquid absorbed in the cover. The cooling system is advantageous in that in the uncharged state, i.e. in the state free from liquid, it comprises a particularly light-weight material, which can easily be transported, stored, and applied and in the charged state it provides no stress, particularly upon the patient. Due to the fact that the cover comprises a particularly flexible material, namely a textile material, the cooling system allows the flexible use for a multitude of applications and simultaneously ensures to achieve an optimal cooling effect by the use as close as possible to the object and/or body, in particular.

Here, the flexible material can be optimally adjusted to the body region of humans and animals to be cooled and only after the respective adjustment then filled, poured, or sprayed with the defined amount of liquid. Here the absorption of liquids occurs particularly rapidly. Due to the particular features of the super absorbing activating means used in the cover and thus also in the cooling system, said cooling can occur within seconds. The absorption of liquids may amount up to a multiple of the weight of the source material of the cooling system. Due to the particular embodiment and/or the features of the super absorbing activation means the liquid applied is absorbed completely, however not released again, even under mechanical pressure. This way, no wetness develops when the cooling system is used, which otherwise would render the body or objects to be cooled and/or their parts becoming moist. This also prevents that measurements, for example necessary medical measurements, from being falsified or prevented due to moisture.

The cooling system according to the invention advantageously comprises a storage container, which accepts the cover charged with liquid. In medicine as well as the field of sports here a product can be provided, which is ready-to-use. This means, the storage container provided in the cooling system according to the invention is stored in the cover already charged with liquid and, upon opening of the storage container, the evaporation and/or vaporization of the liquid begins immediately upon removal of the cover from the storage container and thus the cooling performance is available.

An advantageous further development of the cooling system according to the invention provides therefore that the storage container is provided particularly as a welded plastic container that can be evacuated. Here, the cover is inserted in the non-evacuated state of the container and after evacuation and welding the container is stored. Due to the evacuation and air-tight welding of the plastic packaging a long-lasting shelf life develops for the respectively pre-activated cover, which can be removed when needed in order to be used, for example after injury during sporty activity or in the medical field.

Another advantage of a plastic package is considered the fact that the cover as well as the liquids used for the charge are inserted into the container under sterile conditions or can be sterilized after insertion, so that even in hygienically critical environments, for example in the medical or surgical field, but also in other above-mentioned fields of application a use of the cover according to the invention is possible. In addition to the welded single-use plastic packages, of course it is also possible for the storage container to be embodied as a resealing and/or reusable container made from plastic or metal. Here, too, an option is provided to appropriately sterilize or decontaminate the container in order to allow using it in critical environments as well. For the reusable and resealing containers it is further beneficial that the storage container accepts other liquids for the repeated charging and activation of the cover, stores them, or forwards them like a radiation cooler so that independence can be achieved from an external source for the liquid. For cooling purposes, the cover is removed from the storage container holding the other liquids, used for the cooling application, and after complete evaporation of the liquid accepted in the cover returned into the storage container, in order to again be charged and activated. This process can be repeated many times, as long as liquid is provided in the storage container.

In this context it has proven advantageous for the reservoir to comprise an antibacterial or antimicrobial liquid and/or a respective coating over at least at a portion of the surface of the reservoir facing the cover in order to here ensure respective sterility of the reservoir, on the one hand, and the cover, on the other hand. Further, it has proven beneficial if the content of the reservoir can be disinfected and/or sterilized and the storage container is embodied appropriately such that it withstands several sterilization and/or disinfection cycles.

The release of liquid from the cover and/or the cooling system occurs only by way of evaporation, at no time liquid is released. In order to allow a particularly careful and effective cooling in the cooling system it is considered beneficial for a sensor to be provided for detecting the exterior temperature and the cover temperature. Using the values detected here, upon comparison with the design-related adjustable parameters concerning cooling temperature and cooing period provided by the cooling system, an optimal filling of the cooling system with liquid and/or the optimal cooling period and the cooling intensity can be determined and adjusted.

Here, a temperature display can be allocated to the sensor, which displays the parameters determined at the respective time, so that the status of the cooling system can be detected on a single glance. The cooling system according to the invention preferably comprises a sensor embodied in the form of a color-changing coating or as a thermometer and integrated in the cover and/or the textile fabric.

In addition to a detection of internal parameters of the cooling system, it beneficially also comprises a sensor, which detects in addition to the temperature and moisture also climatic parameters of the environment of the cooling system. Here, particularly the detection of the environmental temperature, relative humidity at various distances from the cooling system, as well as the detection of air flow and its direction and strength are recommended. Then, based on the values determined, a climatic profile can be deducted, which provides the user of the cooling system according to the invention with indications for optimally using the cover and/or the cooling system, in order to achieve a respectively satisfactory cooling performance and cooling effect. From the parameters determined a personal climate index can be calculated for the wearer and/or user of the cooling system, which among other things can also be used for measuring the individual stress, which then offers the chance via punctually precise and/or need-based cooling to achieve a reduction of said stress factors and thus ensuring the well-being of the user or wearer of the cooling system.

The invention also includes the use of a mixture of alcohol and water for charging a cover as mentioned above, and/or for the use in a cooling system, particularly for the use within the scope of a medically required controlled and monitored cooling of humans and animals and/or a cooling system respectively equipped with a sensor for detecting the exterior temperature and the cover temperature, as described above.

Preferably the mixture is here applied on the cover and/or filled into the cover or into a textile fabric provided in the cover or it is charged appropriately with said mixture. The charge and/or filling can either occur via appropriate connections to the cover or such that the entire cover and/or the textile fabric is immersed in a respective mixture, inserted, or sprayed therewith, with here then absorption occurs of the mixture by the cover or the textile fabric. The mixture provided for use preferably comprises alcohol from 1 to 70% by volume, beneficially from 5 to 50% by volume, however particularly from 10 to 30% by volume and water ranging from 30 to 99% by volume. Depending on the purpose for use, here the respective ratios can be varied.

It is considered advantageous for the alcohol to be selected from a group comprising ethanol, isopropanol, or mixtures thereof. Additionally, in a preferred embodiment of the use there is the option to provide the alcohol-water mixture with an additive, here particularly representing an ethereal oil, a fragrance, an aromatic, a repellant (either synthetic or natural), or a denaturant and the portion of the respective additive ranging from 0.1 to 5% by volume. The additive is here not limited to the use of a single adjuvant, rather there is the option that the additives are added in the form of respective mixtures or that the alcohol-water mixture comprises all of the substances mentioned as additives.

The use according to the invention is further characterized in the water being selected from a group comprising tap water, mineralized water, distilled water, demineralized water, or ultrapure water, allowing the use for respectively sensitive applications, for example in the medical field. The mixture suitable for the use according to the invention can additionally or alternatively to the already mentioned additives comprise an adjuvant in the form of biocides, fungicides, virucides, repellants, or antimicrobial and/or antibiotic substances or contain substances allowing a renewal, refreshing, or production of a special finishing or providing the cover with additional functions, the latter substances can also be used as an alternative for alcohol portions of the alcohol-water mixture and then mixed to the water at the volume portion described in this context. The use of mixtures of refreshing substances such as alcohol and/or other activation means or mixtures as described above, is also possible for finishing. The portion of the respective additives or mixtures ranges here are beneficially from 0.1 to 5% by volume. By the above-mentioned substances the use of the alcohol-water mixture is possible in fields of application, which set particular requirements for hygiene. Furthermore, by the respective use improved healing is possible, for example by the use of the cover according to the invention for wound covering. The respective additives therefore expand the range of application of the cover according to the invention and/or contribute to a more specific use.

The invention additionally comprises a piece of clothing, particularly representing a piece of outerwear, which serves as a cover as described above. The piece of clothing, accessory, suspenders, protective clothing, tarp, blanket, ceiling and roof construction, medical product, surgery blanket, pulse cooler, scarf, cooling tape, cooler, bandage, foot and joint bandage, orthotic, facial mask, eye mask, stocking, pantyhose, head covering, cover, particularly building, machine or equipment cover, awning, cellulose, sun roof, covering tarp, and/or protective covering tarp or equipment for the protection from high temperatures, bag, tote, backpack and/or other sports or outdoor product, sports jersey, sports attire, underwear storage, cooling product for animals during transport, or the like comprise several areas, with a textile fabric being provided here as described above, at least in a first section. Here, the textile fabric arranged in the first area of the piece of clothing preferably comprises a super absorbing activation and is particularly suited for cooling after being charged with liquid. Furthermore, the piece of clothing according to the invention comprises at least one second area, in which also a textile fabric is arranged, however this is not mandatory, which here shows a lower cooling effect or none at all, because particularly no super absorbing polymers are arranged in the textile fabric or no textile fabric. An embodiment of the piece of clothing according to the invention provides that the first area of the piece of clothing, equipped with the super absorbing activated textile fabric, can be separated from the second area, not showing any cooling effect. Additionally, there is also the option that the areas of the piece of clothing not equipped with the super absorbing activated textile fabric remains arranged in the piece of clothing itself, and thus avoids areas of the body, in which no cooling is provided and/or medically recommended. The arrangement of a super absorbing activated textile fabric in pieces of clothing leads to an increase of the thickness of said piece of clothing, particularly after the charging with liquid. In order to achieve and/or maintain a compensation and an even surface structure and/or even thickness/height of the piece of clothing it is also possible to arrange a textile fabric in the second area, which shows the same thickness/height as the textile fabric that can be activated, and which contributes that the piece of clothing shows a homogenous appearance. A respective embodiment is not mandatory, though. The embodiment of the piece of clothing having several areas that can be separated or are continuous allows for example a punctual or sectional cooling of certain body regions. This shall be explained in an example:

It has shown for example that a cooling of certain body parts can contribute to an increased performance of athletes. This cooling can already be achieved via the above-described cooling effect of the super absorbing activated textile fabric. If such a piece of sports attire was completely equipped with the activated textile fabric the entire body of the athlete would be cooled. However, this has proven disadvantageous in certain body parts, which under cooling tend to inflammations, as is the case for example in the kidney area. Thus, when a partial cooling of the body of the athlete is provided, particularly in the area of the chest or the upper back, textile fabrics may serve for cooling and thus can be activated or be ready for activation. The area separable or separated therefrom, for example in the area of the kidney or the pelvis of the athlete, would then be less thick, if the textile fabric was arranged in the upper area of the sports attire only, and thus resulted in an uneven appearance of the piece of clothing. Here, the arrangement of non-activated textile fabric can occur in the second area of the piece of clothing and thus a homogenous surface and a continuous appearance is achieved. Additionally, there is the option that the part of the piece of clothing not equipped with the cover and/or the textile fabric is separated therefrom and during activation protected from becoming wet or remains at the piece of clothing and only covers the sections to be cooled.

It is considered advantageous when the first part of the textile product can be connected to the second or other parts of the textile product via one or more connection means. Here, particularly buttons, push buttons, Velcro, snaps, plug connections, or zippers can be used as connection means, via which the separation and connection of the areas of the pieces of clothing can be realized.

It is considered an advantage of the invention in its above-mentioned embodiments that here a controllable, individual, and temperature dependent cooling of objects, persons, and animals is provided, which on the one hand can be realized independent from devices by physical evaporative cooling and on the other hand can be used locally independently and is easily transported. Due to the embodiment of the objects and devices according to the invention, said invention allows a quick readiness for use, lasting cooling effects ranging from hours to even days, as well as a professional cooling for a multitude of medical indications. In particular in the medical field, the cooling can be combined with medical and tele-medical applications. Due to the embodiments of the invention considered advantageous the textile fabric provided and/or the cover equipped therewith is embodied washable and can be sterilized and is thus reusable. Due to the independence from devices and the simple cooling via the utilization of the physical evaporative cooling additionally the invention considerably reduces the $CO_2$-output during the cooling process. The use of a device-independent, locally independent, and easily transported system additionally lowers the costs for use of cooling, and particularly in the context with a medical application of said cooling, also the health care costs. Due to the fact that the cover also included in the invention and/or the piece of clothing comprising the cover is embodied very light-weight in the uncharged state they are not stressing the wearer and thus increase his/her quality of life, yet they ensure the perhaps necessary, sometimes life-saving cooling.

In one example, the design of the composition of the textile fabric according to the invention shall be described, suitable for the use in the above-mentioned objects and articles. The values listed shall only be considered examples of a possible embodiment of the textile fabric according to the invention, and represent no limits of the scope of protection sought for the invention. A textile fabric is presented comprising a polyester fleece. An exemplary textile fabric comprises a polyester fleece, made from fibers produced in a melt spinning method. The polyester solution is here provided first in a liquid form and is ejected from a spinning nozzle. After the polyester material has exiting the spinning nozzle it cures while cooling at the air and here forms, also in connection with the additional impingement of an air flow, a fiber indefinite in principle. At the end of the air flow the fiber hits a sieve belt, with suction being connected thereto. The fibers exiting the nozzles are arbitrarily arranged on the sieve belt and form a fleece, here. Upon reaching a certain fleece thickness and/or a respective weight in reference to the area amounting to 100 g/m$^2$ the fleece formed is removed from the sieve belt and provided for further processing. Here, it is not intended to perform the impingement of the fleece with a super absorbing polymer. In the exemplary embodiment, the super absorbing polymer is provided as a powder comprising particles. In order to now perform a connection between the super absorbing polymer particles and the fleece, said fleece is first coated at both sides with an adhesive substance. This occurs by way of spraying the adhesive onto the polyester fleece. The spraying occurs via nozzles arranged on a jet beam, guided at a constant distances over the fleece and/or its surface. Here, the adhesive sprayed on partially penetrates into the still loosely stacked crude fleece and this way also results in a coating of the fibers located at the inside of the fleece. The adhesive used preferably relates to an aqueous dispersion of copolymerisates based on styrene or acrylic ester, as known for example from the paper production under the product name Acronal™. In order to achieve a particularly good connection between the super absorbing polymer particles and the polyester fleece, here 20 g/m$^2$ adhesive is applied on the fleece. After the application of the adhesive the coating of the fleece occurs with super absorbing polymer particles. Here, it is provided that 400 g particles per m$^2$ fleece is applied thereon and/or incorporated therein. Due to the prior treatment of the fleece with an adhesive said fleece shows an adhesive surface and thus can bond with the particles. Based on the use of 400 g super absorbing polymer particles per m$^2$ fleece the portion of super absorbing activation of the fleece amounts to a weight ratio in reference to the area of 400% of the initial fleece material. In addition to spraying the adhesive onto the fleece material there is also the option to apply the adhesive onto the fleece in a so-called Foulard method. Here the fleece is pulled through a so-called foulard belt containing an adhesive. The adhesive is subsequently compressed so that only a predetermined amount of adhesive remains in the fleece. Here, the fibers forming the fleece represent fibers with a grist of yarn of 2-5 dtex. Of course, there is also the option to select higher or lower grist of yarns. The grist of yarn shall be selected depending on the ultimate purpose for use of the finished, activated fleece. Overall, the formed textile fabric therefore shows a weight per area of 520 g/m$^2$. Due to the fact that 400 g super absorbing polymer is used, which can absorb up to thousand fold its weight in liquids here, up to 400,000 g water, i.e. up to 400 liters water per m2 can be stored in the textile fabric presented as an exemplary embodiment.

In another embodiment of the textile fabric according to the invention the fleece shows a weight per area ranging from 50 to 100 g/m$^2$, preferably approximately 50 to 80 g/m$^2$, and a portion of super absorbing activation, particularly super absorbing polymers with a weight per area ranging from 50 to 400 g/m$^2$, preferably approximately 160 to 240 g/m$^2$, particularly approximately 200 g/m$^2$+/−10%. If applicable, in order to improve the adhesion of the super absorbing polymers to the fleece preferably embodied as a polyester fleece, an adhesive is used, for example based on a polyacrylic acid, which is applied with a weight per area from 5 to 20 g/m$^2$ on one or two sides of the fleece, particularly sprayed on or applied using a foulard process.

This results in a textile fabric according to the invention with a weight per area ranging from 100 to 700 g/m$^2$.

In this context it is particularly pointed out that all features and characteristics described in reference to the device but also all processes with regards to the formulation of the method according to the invention can be transferred and used in the sense of the invention and are considered also disclosed, here. The same also applies inversely, which means structural thus device-related features mentioned only in reference to the method can also be considered within the scope of the device claims and thus be claimed here and are also considered included in the invention and the disclosure.

DETAILED DESCRIPTION OF THE PREFERRED EMBODIMENTS

Figure 1:
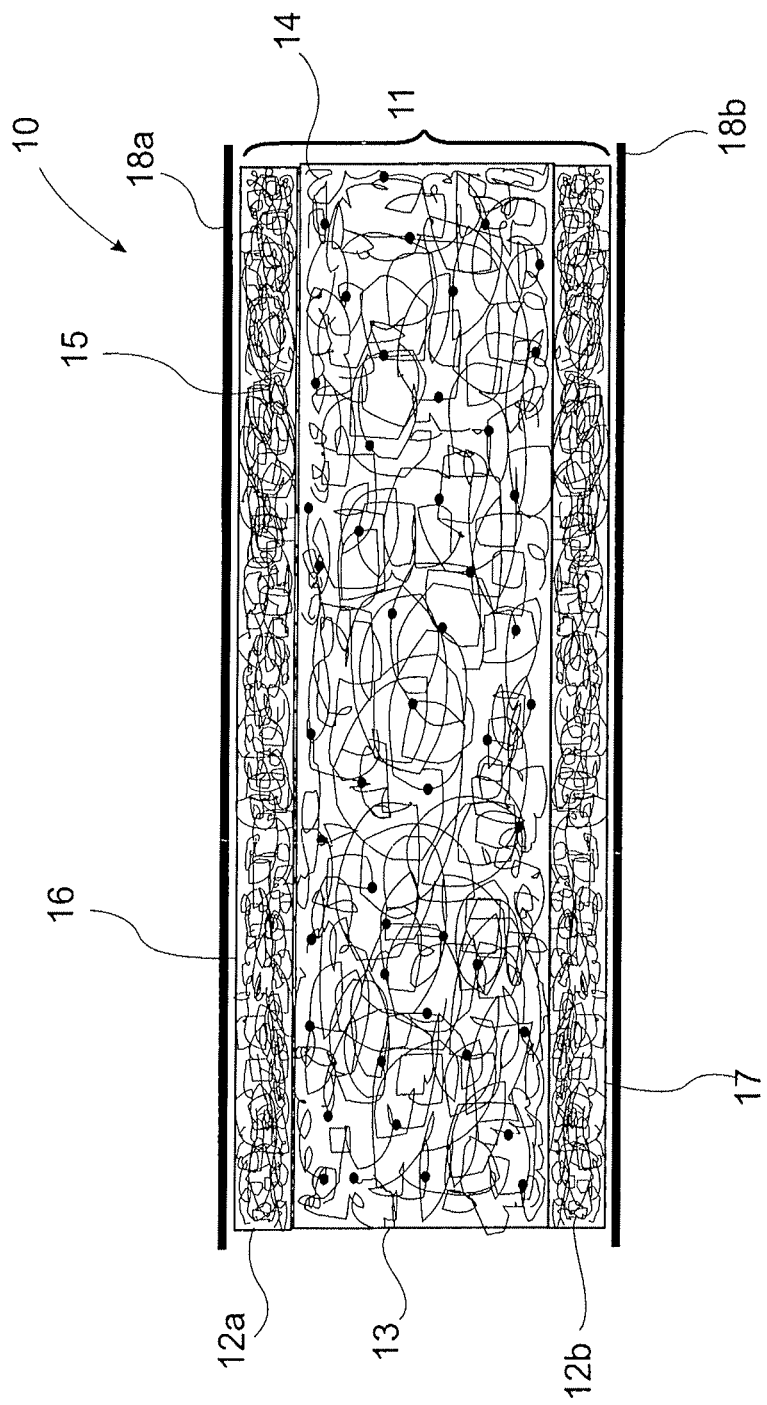
FIG. 1 a cross-section of a cover equipped with the textile fabric according to the invention, FIG. 2 a cross-section of a cover equipped with the textile fabric according to the invention in the charged state, FIG. 3 a cross-section of a cover equipped with another embodiment of the textile fabric according to the invention.

The cover 10 shown in FIG. 1 comprises in its interior a textile fabric 11, which shows an overall three-layered design. The two exterior layers 12*a*, 12*b* are made from the same material as the inner layer 13, which however shows a modified structure and thickness. In the exemplary embodiment of FIG. 1 the textile fabric 11 is formed by a random-structured fleece, which comprises fibers 14 stacked in an uncontrolled fashion. In the exemplary embodiment, the fibers 14 were formed in a melt spinning process and comprise thermoplastic polymers. Arranged in the fleece material of the textile fabric 11, there are particles 15 made from super absorbing polymers, which are chemically bonded to the fibers 14 and permanently adhere thereto. The connection of particles 15 and fibers 14 occurred by impinging the textile fabric 11 with an interlacing means. This first causes an interlacing of the super absorbing polymer and/or its precursors and during said process a bonding occurs between the fibers 14 and the particles 15. The particles 15 are penetrated by the fibers 14. In addition to the super absorbing polymers in the form of particles 15, of course it is also possible that the fibers 14 are coated with super absorbing polymer and/or are entirely made from super absorbing polymer. In addition to the entire formation of the fibers 14 from super absorbing polymer, there is also the option that the super absorbing polymer is implemented in the fibers 14 and/or inserted in the source polymer solution, from which the fibers 14 are spun.

The formation of the fleece, which ultimately forms the textile fabric 11, occurs by applying the fibers 14 ejected from nozzle onto a sieve belt or another area (not shown) impinged with a vacuum. Additionally, in order to improve the features of the fleece and/or the features of the textile fabric 11 needling or any other reinforcement of the textile fabric 11 may be performed. Here, for example during the needling process, individual fibers from a first surface 16 are inserted at least partially into the body of the fleece and this way reinforces it.

In the exemplary embodiment of FIG. 1, only a surface treatment of the crude fleece occurred, so that here at the first upper surface 16 and the second lower surface 17 layer of fleece is formed, which in reference to the remaining body of the fleece, i.e. in reference to the inner layer 13, shows a reinforced structure. Here the formation of the exterior layers 12a, 12b can occur by thermal, chemical, or mechanical treatment of the fleece and/or the crude fleece directly after its formation or also at a later time. For a mechanical reinforcement a needling or water jet method is used in order to perform an alignment of some of the fibers 14 of the exterior layer 12a, 12b. The ultimate thickness and thus also the density of the exterior layers 12a, 12b is determined by the depth of the needles and/or the water jets penetrating into the crude fleece.

The number of needles and/or water jets penetrating the fleece also determines the density and reinforcement. In a chemical process, the exterior layers 12a, 12b of the fleece are treated with a substance causing a softening of the fibers 14 and/or the fiber jackets (not discernible) and, upon rehardening of the fibers, the connection and/or the "melting together" of the fibers pretreated in this manner is performed.

In addition to the above-mentioned mechanical and chemical methods a thermal treatment of the crude fleece is also possible. This is particularly suitable when the fleece body and/or the crude fleece is formed from thermoplastic polymers, i.e. when the fibers 14 comprise a thermally liquefiable polymer mixture. Here, by impinging the crude fleece with a heated gas flow or with water vapors or also by applying or rolling the fleece with heated rollers a melting of the fibers 14 and/or the fiber jackets can be performed. Prior to cooling the crude fleece treated in this manner a contacting and/or adhesion of the liquefied and/or softened fiber jackets occurs, which after cooling in this position remain permanently melted to each other. By the intensity and duration of the impingement of the crude fleece here the penetrating depth and/or the portion of the fibers 14 can be defined, which are subjected to the melting method and thus the thickness and density of the exterior layers 12a, 12b can be predetermined, if necessary. The transition to the inner layer 13 can here be embodied gradually. In addition to the formation of the exterior layers 12a, 12b from the crude fleece in a single processing step, of course the arrangement of additional material webs can also occur on the inner layer 13. These material webs then can also be embodied without any super absorbing functions and absorbing the inner layer 13 of the textile fabric 11 in its interior. In addition to the arrangement of additional fleece webs as exterior layers 12a, 12b there is also the option to coat and/or cover the textile fabric 11 with overlays 11a, 11b embodied as membranes or films. Via these overlays 18a, 18b an additional function can be established of the textile fabric 11 and/or the cover 10 including or forming it. Here, the overlays 18a, 18b may be activated to be water tight, dirt-repellant, or activated in another suitable fashion. Simultaneously there is also the option for the overlays 18a, 18b to be embodied as coatings, which are applied only on the first and second surface 16, 17 or only on one of the surfaces 16, 17. Then, the coating can also provide an additional activation of the textile fabric 11 or the entire cover 10. For example, there is the option to form the entire coating from a liquid-tight, flame-resistant, self-cleaning, dirt-repellant, biocidal, antiviral, or antimicrobial material.

Another option for activating the cover 10 and/or the textile fabric 11 comprises to integrate the respective activation means already into the fleece, i.e. particularly into the inner layer 13. This may occur during the formation of the crude fleece. In order to here allow performing a biocidal activation of the textile fabric 11, individual fibers 14 may be embodied from a silver material or with a silver coating. In addition to the activation of individual fibers 14 of the textile fabric 11, of course it is also possible to integrate additional particles, for example nano-particles, into the textile fabric 11, which then provide the desired additional features of the textile fabric 11.

In particular, the liquid-tight, self-cleaning, and/or dirt-repellant activation represents a finishing of the first or second surface 16, 17 of the textile fabric 11 and/or the cover 10. This activation, i.e. the respective coating, can here occur by way of spraying or brushing the textile fabric 11 and/or the cover 10 with a respective material. Additionally, there is the option for the entire textile fabric 11 and/or the entire cover 10 to be immersed in a solution, which comprises the respective means for functionalization and/or activation. After the final drying, a complete coating is ensured. The textile fabric 11 of FIG. 1 comprises additional overlays 18a, 18b to form the cover 10, encasing it. These overlays 18a, 18b are here embodied such that they allow the penetration of liquids into the textile fabric 11, however only allow the emission of water vapor from the textile fabric 11. For this purpose, the overlays 18a, 18b comprise appropriate pores (not shown), which have a diameter smaller than the particles 15 arranged in the textile fabric 11 and/or particularly in the inner layer 13. This is particularly important when individual particles 15 or particle parts separate from the fibers 14, because the size of the pores ensures that the respective particles 15 cannot exit the textile fabric 11 and/or the cover 10. Additionally, it is prevented by the described embodiment of the overlays 18a, 18b that moisture appears at the surfaces 16, 17, which might come into contact with the object and/or body part covered by the cover 10.

Figure 2:
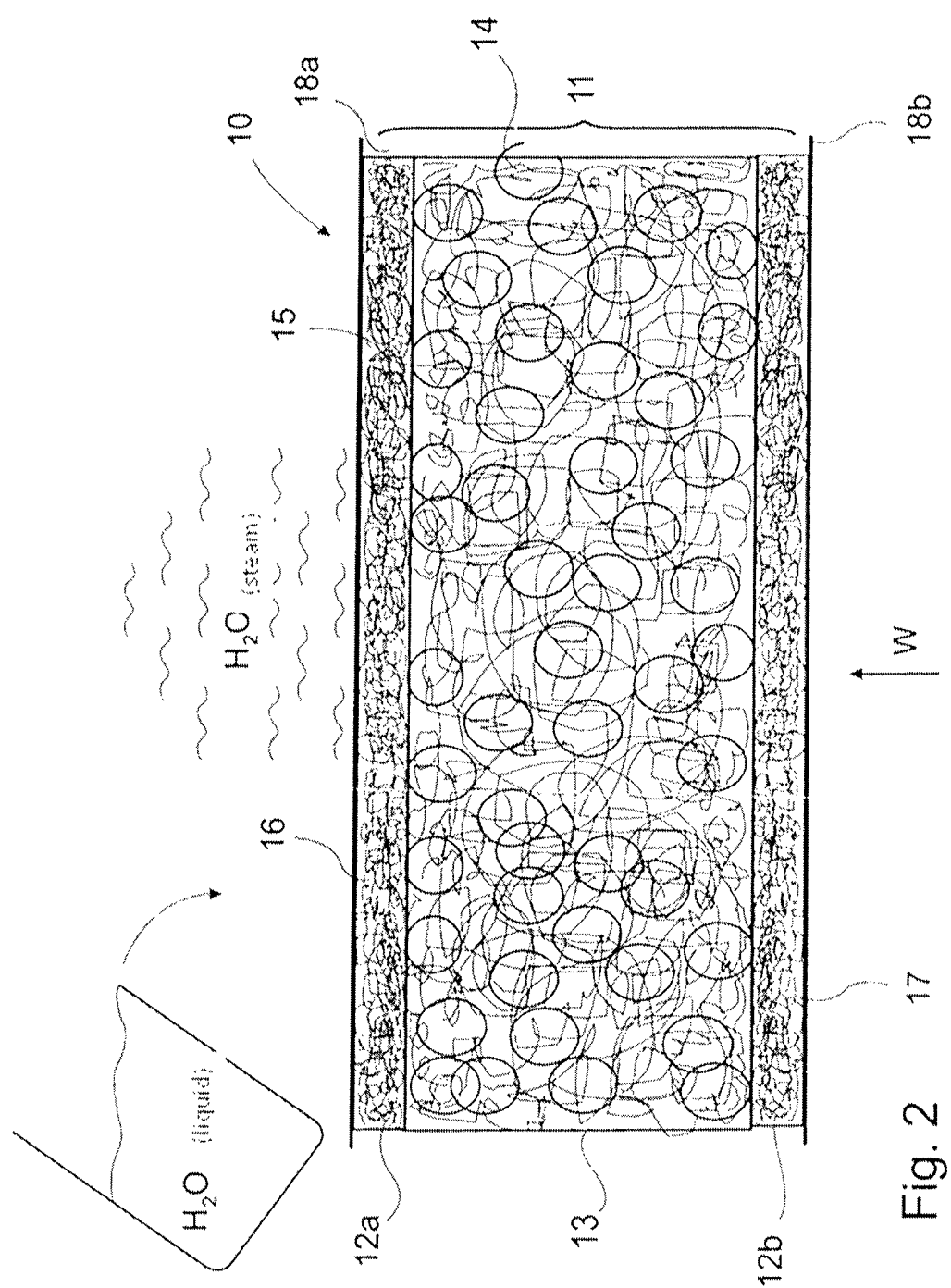

FIG. 2 shows an already described textile fabric 11 in the charged state. The particles 15 made from a super absorbing polymer are clearly discernible in their now swollen state. They are physically, mechanically, or chemically connected to the fibers 14 and adhere thereat permanently. From FIG. 2 a relatively homogenous distribution of the particles 15 is discernible in the textile fabric 11, which leads that hardly any contact points are given between the individual particles 15, thus they can reach their maximal swelling capacity and here the maximal absorption capacity for liquids without being interfered by neighboring particles 15. FIG. 2 shows a pouring of liquid onto the textile fabric 11. In addition to this option of pouring liquid, there is of course also the possibility for spraying the liquid onto the textile fabric 11 or for the entire textile fabric 11 to be immersed in the liquid, so that here a respective absorption of liquids by the particles 15 can occur. In the exemplary embodiment of FIG. 2 plain water is used as the liquid, however the use of alcohol-water mixtures or mixtures of alcohol, water, and/or other additives is also possible, which then simultaneously results in a respective activation or functionalization of the textile fabric 11. In the exemplary embodiment of FIG. 2 an impingement of liquid occurs of the first surface 16 of the textile fabric. Here, the liquid applied penetrates the overlay 18a, embodied as the top layer of the cover 10, which encompasses the exterior layer 12a of the fleece, and is absorbed in the inner layer 13 of the body of the fleece by particles 15 arranged there and homogenously distributed. Then, a thermal treatment of the textile fabric 11 occurs from the second upper side 17 of the textile fabric, for example such that the casing 11 is used as a cover for a heat-releasing device or is placed onto a body. This impingement with heat, shown in the exemplary embodiment by the arrow W, leads to evaporation and/or vaporizing of the liquid reversibly bonded in the particles 15. This evaporation process requires that heat is removed from the covered object and/or body or body part, thus a respective cooling performance or cooling effect develops. The liquid evaporated from the particles 15 exits in the form of water vapor at the upper surface 16 of the textile fabric 11. The overlay 18a embodied as the top layer of the encasing provides for this purpose a respective functionalization, which allows the even emission of water vapor. During the emission of liquid from the particles 15, they are subject to a shrinking process and after the complete release of the liquid they reach the unswollen state shown in FIG. 1. After or already during the evaporation process a renewed charge of the textile fabric 11 with additional liquid can occur, which then leads to a renewed swelling of the particles 15. The textile fabric 11 according to the invention and/or the cover 10 equipped therewith allows such repeated charge and release cycles with liquid and a long-lasting cooling effect achieved in this manner. This cooling effect and/or the previous impingement with liquid is improved such that on the one hand a homogenous distribution of the particles 15 is provided in the textile fabric 11 and on the other hand the sizes of the particles are within a relatively narrow range or diameters, thus the particles 15 show identical features with regards to the speed of absorption and release of the liquid. The permanent bond of the particles 15 with the fibers 14 of the fleece prevents the separation of the particles 15 and their collection, for example in the area of the lower surface 17 of the cover.

Figure 3:
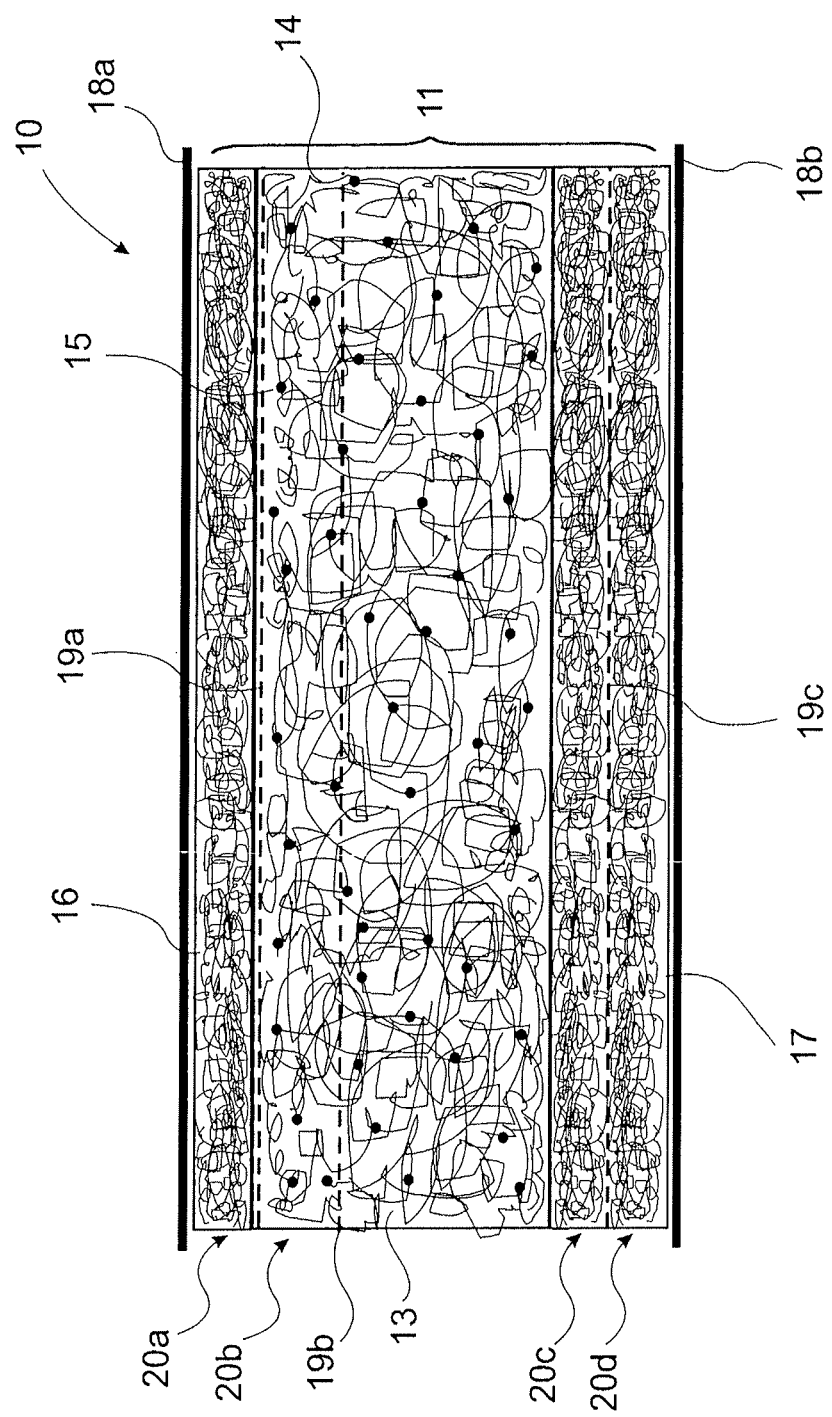

FIG. 3 shows the use of membranes 19a, 19b, 19c in another embodiment of the textile fabric 11 according to the invention. It comprises a total of four layers 20a, 20b, 20c, 20d, which therefore form a multi-layer embodiment of the textile fabric. In addition to the layers of the textile fabric 11 top layers of the cover 10 in the form of overlays 18a, 18b are provided representing the exterior boundary surfaces of the cover 10, and between which the textile fabric 11 is located. In the exemplary embodiment of FIG. 3, the textile fabric 11 comprises an inner layer 13, which is formed by a super absorbing activated fleece. Here, the super absorbing polymers are also provided in the form of particles 15, which are bonded to the fibers 14 and thus permanently fixed in the inner layer 13. The inner layer 13 thus forms an inner layer 20b of the textile fabric. The inner layer is enclosed by additional, not activated layers 20a, 20c, 20d, which in the exemplary embodiment are formed from a fleece material, which shows no super absorbing activation, however allows the penetration of liquids.

The inner layer 13 is separated from the first, upper layer 20a of the textile fabric by a first membrane 19a. Said membrane is embodied like a climate and/or functional membrane and allows the penetration of water vapors, which thus discharge from the inner layer 13 and can penetrate into the upper layer 20a in order to be released therefrom via said overlay 18a into the environment.

Another membrane 19a is arranged in the inner layer 13, serving to ensure an improved distribution of the liquid inserted into the textile fabric.

The inner layer 13 of the textile fabric 11 is limited by two additional layers 20c, 20d, which in turn are separated by an interposed membrane 19c. This membrane 19c is realized such that any penetration of liquid inserted into the textile fabric 11 towards the lower surface 17 of the textile fabric 11 through said membrane 19c is prevented. The use of two layers 20c, 20d causes an additional stabilization of the textile fabric 11 and the cover 10 accepting it. The cover 10 comprises a total of two overlays 18a, 18b considered cover layers, between which the textile fabric 11 is arranged. A respective arrangement can occur, for example by inserting or inlaying the textile fabric 11 between the two overlays 18a, 18b. Additionally, the overlays 18a, 18b overall may form a pocket-like accept for the textile fabric 11, into which it can be inserted, if necessary. The overlays 18a, 18b themselves may show a respective functionalization, in order to provide the enclosure with additional features, which then allow the utilization for most different fields of application. For example, the overlays 18a, 18b, and of course also the overlays 20a, 20c, 20d, and perhaps also the inner layer 13 may comprise a liquid-tight, flame-resistant, spark-resistant, resistant against metal or other embers, dirt-repellant, biocidal, antiviral, UV-blocking, antistatic, repellant, cosmetically effective, medically effective, hydrophilizing, antimicrobial, or electromagnetic radiation shielding or absorbing equipment or finishing and/or coating. This way, a very wide range of application of the cover 10 according to the invention is yielded.

While in FIG. 3 the equipment with a total of three additional membranes 19a, 19b, 19c is shown, of course there is also the option that here only two membranes are provided, encasing the inner layer 13, however additional membranes may also be arranged in the textile fabric 11, of course, which then cause additional compartmenting of the structure of the textile fabric 11 and perform additional protective or distributive functions and/or further improve the absorption or release of liquids. The membranes may be arranged subsequently in the textile fabric, however it is also possible that a respective membrane, for example formed as carriers for the fibers 14 ultimately forming the fleece, is used and covered at one or both sides with respective fibers 14 in the fleece-forming process. Additionally, it is also possible to divide the fleece after its formation so that both halves of the fleece then encase a membrane arranged therebetween. Additionally there is the option to form the textile fabric 11 in a sandwich design, i.e. the individual layers of plies 20a, 20b, 20c, 20d and/or the membranes 19a, 19b, 19c arranged therebetween are composed in a layered structure, which means, for example first a lower layer 20d is provided, which then is covered with a membrane 19c, upon which then another layer 20c is placed upon the membrane 19c. Then, for example, an inner super absorbing activated layer 13 can be applied on the second layer 20c, which in turn is covered with a membrane 19a, limiting the inner layer 13 from another layer 20a, which in the production process is then applied, placed, laid, or adhered on the upper membrane 19a.

The features can be defined for the respective layers, such as speed of liquid absorption and liquid release as well as other mechanic parameters of the textile fabric 11.

By the selection of suitable membranes another functionalization and/or activation of the textile fabric 11 and/or the cover 10 can be achieved. The selection of suitable membranes influences for example the permeability for liquids and/or evaporated liquids. In order to achieve a sealing towards a body to be cooled, for example an impermeable membrane can be used, while the emission of water vapor from the cover 10 and/or the textile fabric 11 can be implemented via partially impermeable, semi-permeable, or selectively permeable and/or in one direction impermeable, unidirectional membranes. Additionally, via the selection of a suitable membrane the mechanical resistance of the cover 10 and/or the textile fabric 11 can also be influenced, because the membranes show the feature to compensate only tensile stress under load and to forward it to its edges.

Another activation or functionalization of the textile fabric 11 and/or the cover 10 can be achieved by the embodiment of the membrane with a defined strength, thickness, or functionality, because here for example via appropriately applied membranes the sealing of the textile fabric 10 can be achieved. Even under aspects of hygiene, the use of membranes has proven advantageous because they allow a particularly easy cleaning of the textile fabric and/or the cover and simultaneously shield the interior of the textile fabric 11 from aggressive cleaning substances.

In FIG. 1 through 3 the insertion of super absorbing polymers into the textile fabric 11 is shown only in the form of particles 15. In addition to this option for impingement, of course there is also the possibility to form the fibers 14 from super absorbing polymer and/or for super absorbing polymer to be embedded in the fibers so that then upon contact with liquid a swelling of the entire fiber occurs. During the swelling process naturally the thickness or height of the textile fabric increases, with this change of shape and/or dimensions occurring within narrow limits due to the homogenous distribution of the super absorbing polymer particles 15 in the textile fabric 11.

The claims included in this application and perhaps those filed subsequently represent attempts for a formulation without any prejudicial limits for obtaining further protection.

In the event it shows during the examination, particularly with regards to prior art, that one or the other feature, although beneficial for the objective of the invention but not of decisive importance, of course a formulation is intended, which no longer includes such a feature, particularly in the main claim.

Additionally, it must be observed that the embodiments and variants of the invention described in the various embodiments and shown in the figures can be arbitrarily combined with each other. Here, one or more features can be arbitrarily exchanged for one another. These combinations of features are also disclosed, here.

The references made in the dependent claims relate to the further embodiment of the objective of the main claim by the features of the respective dependent claim. However, this shall not be understood as a waiver of achieving an independent, objective protection for the features of the dependent claims.

Features previously only disclosed in the description may also be claimed during the proceedings as being of essential importance for the invention, for example for separation from prior art.

Features only disclosed in the description or individual features of the claims comprising a multitude of features may be adopted at any time into the first claim for separation from prior art, namely including when such features are mentioned in the context with other features and/or achieve particularly beneficial results in the context with other features.

The invention claimed is:

1. A textile fabric for repeated use, wherein the textile fabric is configured to be activated when charged with liquid and to provide a cooling effect upon discharging of the liquid, the textile fabric comprising:
   a non-woven fleece material having artificial fibers or artificial filaments and two opposed exterior layers,
   the two opposed exterior layers being liquid pervious for allowing passage of liquids through the two opposed exterior layers towards the artificial fibers or artificial filaments; and
   a super absorbing material configured to permanently connect to the artificial fibers or the artificial filaments,
   the artificial fibers or the artificial filaments of the non-woven fleece material being coated with the super absorbing material, each of the artificial fibers or the artificial filaments are surrounded and encased by the super absorbing material,
   the non-woven fleece material including the two opposed exterior layers is configured to be machine washable and reusable.

2. The textile fabric according to claim 1, wherein the non-woven fleece material, in an absence of the super absorbing material, includes a weight ranging from 50 g/m$^2$ to 120 g/m$^2$.

3. The textile fabric according to claim 1, wherein the non-woven fleece material includes reinforcement fibers penetrating a thickness/height of the non-woven fleece material.

4. The textile fabric according to claim 1, wherein the artificial fibers or the artificial filaments have a yarn fineness ranging from 0.1 dtex to 20 dtex.

5. The textile fabric according to claim 1, wherein at least one of the two opposed exterior layers includes a flame-resistant, fire-resistant, spark resistant, resistant to splashing metal or embers, liquid metal repellant, self-cleaning, dirt-repellant, biocidal, antiviral, UV-blocking, antistatic, repellant, cosmetically effective, medically effective, antimicrobial, antibacterial, antibiotic, or electromagnetic radiation absorbing, shielding, coating or finishing.

6. A cover of comprising two or more parts, wherein at least one part of the two or more parts of the cover is the textile fabric according to claim 1.

7. The cover according to claim 6, wherein another part of the at least one part of the cover contacts the textile fabric.

8. The cover according to claim 6, wherein at least one part which is the textile fabric is fixed at or in the cover by adhesion, sewing or by a connection means.

9. A cooling system comprising a cover according to claim 6, wherein the cover is configured to monitor cooling of people, animals and/or objects.

10. The textile fabric according to claim 1, wherein the fleece material and the two opposed exterior layers together have a dry weight of 200 g/m² to 1500 g/m².

* * * * *